US012582593B2

(12) United States Patent
Biesbrock et al.

(10) Patent No.: US 12,582,593 B2
(45) **Date of Patent: *Mar. 24, 2026**

(54) ORAL CARE COMPOSITIONS FOR GUM HEALTH

(71) Applicant: The Procter & Gamble Company, Cincinnati, OH (US)

(72) Inventors: Aaron Reed Biesbrock, Maineville, OH (US); Yunming Shi, Beijing (CN); Ross Strand, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/890,498

(22) Filed: Aug. 18, 2022

(65) Prior Publication Data

US 2023/0233438 A1 Jul. 27, 2023

(30) Foreign Application Priority Data

Aug. 23, 2021 (WO) ................ PCT/CN2021/113981

(51) Int. Cl.
*A61K 8/67* (2006.01)
*A61K 8/34* (2006.01)
(Continued)

(52) U.S. Cl.
CPC .............. *A61K 8/671* (2013.01); *A61K 8/345* (2013.01); *A61K 8/44* (2013.01); *A61K 8/64* (2013.01); *A61K 8/922* (2013.01); *A61Q 11/00* (2013.01)

(58) Field of Classification Search
CPC .......... A61K 8/671; A61K 8/345; A61K 8/44; A61K 8/64; A61K 8/922; A61Q 11/00
See application file for complete search history.

(56) References Cited

U.S. PATENT DOCUMENTS 6,492,326 B1 12/2002 Robinson
6,740,327 B2 5/2004 Yu et al.
(Continued)

FOREIGN PATENT DOCUMENTS

CA 2710650 A1 8/2009
CA 3095048 A1 10/2019
(Continued)

OTHER PUBLICATIONS

PCT Search Report and Written Opinion for PCT/CN2021/113981 dated Feb. 10, 2022, 15 pages.
(Continued)

*Primary Examiner* — Marianne C Seidel
*Assistant Examiner* — Amanda Michelle Petritsch
(74) *Attorney, Agent, or Firm* — John G. Powell; Elizabeth Conklin

(57) ABSTRACT

An oral care composition with retinoid compound, amino acid, and/or olive oil. An oral care composition with retinoid compound, a pentapeptide, such as palmitoyl KTTKS [SEQ ID NO. 2], and/or an olive oil. Methods of preventing gingival recession, stopping gingival recession, reversing gingival recession, decrease gum recession, increase gingival barrier protection, promoting collagen synthesis, promoting extracellular matrix synthesis, increasing gum resilience, increasing epidermal thickness and/or promoting fibrillin synthesis, in an oral cavity of an animal by contacting the oral care compositions with at least one surface of the oral cavity.

17 Claims, 5 Drawing Sheets

Specification includes a Sequence Listing.

(51) Int. Cl.

| | |
|---|---|
| *A61K 8/44* | (2006.01) |
| *A61K 8/64* | (2006.01) |
| *A61K 8/92* | (2006.01) |
| *A61Q 11/00* | (2006.01) |

(56) References Cited

U.S. PATENT DOCUMENTS

| | | | | |
|---|---|---|---|---|
| 8,871,717 | B2 | 10/2014 | Osborne | |
| 9,616,011 | B2 | 4/2017 | Osborne | |
| 10,435,532 | B2 | 10/2019 | Layman | |
| 10,493,009 | B2 | 12/2019 | Ha | |
| 10,588,833 | B2 | 3/2020 | Baig | |
| 2004/0175347 | A1 | 9/2004 | Bissett | |
| 2005/0019356 | A1 | 1/2005 | Bissett | |
| 2006/0018867 | A1* | 1/2006 | Kawasaki | A61K 8/898 424/70.122 |
| 2007/0053851 | A1 | 3/2007 | Maillan et al. | |
| 2007/0196296 | A1* | 8/2007 | Osborne | A61K 8/63 424/61 |
| 2009/0202454 | A1 | 8/2009 | Prencipe et al. | |
| 2009/0232915 | A1 | 9/2009 | Schmaus et al. | |
| 2010/0305168 | A1 | 12/2010 | Robinson et al. | |
| 2012/0028916 | A1* | 2/2012 | Fournial | A61K 8/498 514/33 |
| 2015/0297500 | A1 | 10/2015 | Robinson et al. | |
| 2016/0271022 | A1 | 9/2016 | Giniger | |
| 2016/0279039 | A1 | 9/2016 | Giniger | |
| 2017/0100312 | A1 | 4/2017 | Prencipe | |
| 2017/0367956 | A1 | 12/2017 | Chen | |
| 2017/0368375 | A1 | 12/2017 | Chen | |
| 2019/0247540 | A1 | 8/2019 | Hug | |
| 2019/0298634 | A1 | 10/2019 | Strand | |
| 2020/0016089 | A1 | 1/2020 | Chiou | |
| 2020/0390676 | A1 | 12/2020 | Strand | |
| 2020/0390677 | A1 | 12/2020 | Strand | |
| 2020/0390801 | A1 | 12/2020 | Strand | |
| 2021/0007948 | A1 | 1/2021 | Baig | |
| 2022/0401343 | A1 | 12/2022 | Bascom et al. | |
| 2022/0409512 | A1 | 12/2022 | Bascom et al. | |

FOREIGN PATENT DOCUMENTS

| | | | |
|---|---|---|---|
| CA | 3095052 | A1 | 10/2019 |
| CN | 1610535 | A | 4/2005 |
| CN | 1713886 | A | 12/2005 |
| CN | 102548535 | A | 7/2012 |
| CN | 106176306 | A | 12/2016 |
| CN | 106456560 | A | 2/2017 |
| CN | 106619332 | A | 5/2017 |
| CN | 107427423 | A | 12/2017 |
| CN | 108888770 | A | 11/2018 |
| CN | 108939079 | A | 12/2018 |
| CN | 107670021 | B | 9/2020 |
| CN | 112121157 | A | 12/2020 |
| EP | 1393710 | A1 | 3/2004 |
| EP | 1708725 | B1 | 5/2016 |
| JP | 2020002131 | A | 1/2020 |
| KR | 20150010550 | A | 1/2015 |
| KR | 20170065944 | A | 6/2017 |
| WO | 2019180530 | A1 | 9/2019 |
| WO | 2019183876 | A1 | 10/2019 |
| WO | 2019183886 | A1 | 10/2019 |
| WO | 2019183888 | A1 | 10/2019 |
| WO | 2020047395 | A1 | 3/2020 |
| WO | 2020137417 | A1 | 7/2020 |
| WO | 2020139784 | A1 | 7/2020 |
| WO | 2020249040 | A1 | 12/2020 |
| WO | 2020249042 | A1 | 12/2020 |
| WO | 2020249045 | A1 | 12/2020 |

OTHER PUBLICATIONS

Anonymous: "Active Mouthwash Gel", Database GNPD [Online] Mintel; Nov. 26, 2019, 2 pages.

Anonymous: "Gengigel Oral Hygiene Range", Database Gnpd [Online] Mintel; Feb. 17, 2005, 2 pages.

Anonymous: "Lamiophlomis Rotata Xue Yu Whitening Toothpaste with Salt", Database GNPD [Online] Mintel; Feb. 7, 2014, 3 pages.

Anonymous: "Lemon Flavoured Gum Protection Biological Peptide Toothpaste", Database GNPD [Online] Mintel; Jan. 30, 2019, 4 pages.

Anonymous: "Mint Freshness Toothpaste", Database GNPD [Online] Mintel; Feb. 25, 2020, 4 pages.

Anonymous: "Periodontal Vitamin Toothpaste", Database GNPD [Online] Mintel; Dec. 10, 2019, 3 pages.

Anonymous: "Toothpaste", Database GNPD [Online] Mintel, Jan. 29, 2001, 2 pages.

Anonymous: "Toothpaste", Database GNPD [Online] Mintel; Nov. 16, 2018, 3 pages.

Anonymous:"Gum-Protection Toothpaste", Database GNPD [Online] Mintel; Jan. 2, 2007, 2 pages.

Anonymous; Database GNPD Mintel, "Active Mouthwash Gel", XP055809294, Database accession No. 7062823, dated Nov. 26, 2019, 02 Pages.

Anonymous; Database GNPD Mintel, "Gum Protection Toothpaste", XP055809798, Database accession No. 636724, dated Jan. 2, 2007, 02 Pages.

Anonymous; Database GNPD Mintel, "Lamiophlomis Rotata Xue Yu Whitening Toothpaste with salt" XPO55809281, Database accession No. 2305848, dated Feb. 7, 2014, 03 Pages.

Anonymous; Database GNPD Mintel, "Lemon Flavored Gum Protection Biological Peptide Toothpaste", XP055809305, Database accession No. 6304363, dated Jan. 30, 2019, 04 Pages.

Anonymous; Database GNPD Mintel, "Toothpaste", XP055809295, Database accession No. 85453, dated Jan. 29, 2001, 02 Pages.

Anonymous; Database GNPD Mintel, "Periodontal Vitamin Toothpaste", XP055809797, Database accession No. 7088753, dated Dec. 10, 2019, 03 Pages.

* cited by examiner

ORAL CARE COMPOSITIONS FOR GUM HEALTH

SEQUENCE LISTING

This application contains a Sequence Listing which has been submitted electronically in XML format and is hereby incorporated by reference in its entirety. The XML copy, created on Feb. 28, 2023, is named 16109_Sequence_Listing and is 4,710 bytes in size.

FIELD OF THE INVENTION

The present invention relates to oral care compositions comprising retinoid compound, olive oil, and optionally amino acid. The present invention also relates to leave-on oral care compositions comprising retinoid compound, amino acid, and olive oil. The present invention also relates to leave-on oral care compositions comprising retinoid compound, polypeptide, and olive oil. The present invention also relates to emulsions comprising retinoid compound, olive oil, and optionally amino acid/polypeptide.

BACKGROUND OF THE INVENTION

The oral epithelial barrier separates the host from the environment and provides the first line of defense against pathogens, exogenous substances and mechanical stress. The oral epithelial barrier includes underlying connective tissue and a stratified keratinized epithelium with a basement membrane, whose cells undergo terminal differentiation resulting in the formation of a mechanically resistant surface. Gingival keratinocytes are connected by various transmembrane proteins, such as tight junctions, adherens junctions, and gap junctions, each of which has a specialized structure and specific functions. Bacteria secrete compounds detrimental to host defenses, endotoxins and exotoxins, free radicals and collagen-destroying enzymes, leukotoxins, bacterial antigens, waste products, and toxic compounds. Disruption of the gingival epithelial barrier, and the subsequent penetration of exogenous pathogens into the host tissues, triggers an inflammatory response, establishing chronic infection. If this elegant and well-adapted defense system is overwhelmed by bacterial virulence and prolonged inflammation, tissue destruction can be mediated by host cells following stimulation with cytokines and bacterial products. The junctional epithelium migrates apically on the root surface and activates collagen destruction, which eventually leads to periodontal pocket formation and gum recession.

Gum recession is the loss of gum tissue, which attaches to the tooth at the cementoenamel junction (CEJ), which is a slightly visible border that distinguishes the crown of the tooth, which is covered by enamel, and the root of the tooth, which is covered by cementum. When gums recede, gaps can form between the gum tissue and the CEJ, thereby exposing more of the cementum of the tooth's root. Bacteria and debris can build up in the formed gap between the tooth's surface and the gum tissue.

Gum recession can expose the tooth's root, lead to increases in cavities or periodontal disease leading to potential tooth loss, and can be viewed as aesthetically unpleasant. While a dental professional can remove accumulated bacteria, plaque, and/or tartar mechanically, the only way to treat severe gum recession is gum grafting surgery, which can be painful, inconvenient, and expensive. Accordingly, there is a need for a non-surgical treatment option for individuals with high risk of developing or currently diagnosed with gum recession.

SUMMARY OF THE INVENTION

Disclosed herein is a leave-on oral care composition comprising retinoid compound, amino acid, and olive oil.

Disclosed herein is a leave-on oral care composition comprising retinoid compound, peptide, and olive oil.

Disclosed herein is an oral care composition comprising retinoid compound, amino acid, and olive oil, wherein the composition is a leave-on oral care composition, unit-dose oral care composition, an emulsion composition, a dispersion, a dentifrice, tooth gel, subgingival gel, mouth rinse, mousse, foam, mouth spray, lozenge, chewable tablet, chewing gum, tooth whitening strips, floss and floss coatings, breath freshening dissolvable strips, denture care products, denture adhesive products, or combinations thereof.

Also disclosed herein are kits comprising the disclosed compositions and a suitable delivery carrier.

Also disclosed herein are methods of use of the disclosed compositions to improve the health of the gums in an oral cavity.

Also disclosed herein is a method of preventing gingival recession, stopping gingival recession, reversing gingival recession, decrease gum recession, increasing gingival barrier protection, promoting collagen synthesis, promoting extracellular matrix synthesis, increasing gum resilience, increasing epidermal thickness and/or promoting fibrillin synthesis, or combinations thereof in an oral cavity of an animal comprising contacting the disclosed oral care compositions with at least one surface of the oral cavity.

DETAILED DESCRIPTION OF THE INVENTION

The present invention is directed to oral care compositions comprising retinoid compound, amino acid/peptide, and olive oil, such as PEGylated olive oil. Additionally, the present invention is directed to a method of preventing gingival recession, increasing gum resilience, stopping gingival recession, reversing gingival recession, promoting collagen synthesis, promoting fibrillin synthesis, or combinations thereof in an oral cavity of an animal comprising contacting the disclosed oral care compositions with at least one surface of the oral cavity.

Aging has a negative physical impact on many tissues including epithelial tissues such as skin and gingiva. Through a cross-study analysis, common molecular features responsible for the loss of function in aging skin and gingiva were identified. Such features have been well studied in skin and have been pharmacologically targeted to improve aging related damage. However, as described herein, the gingiva has not been well studied. Unexpectedly, when the ingredients found to be successful in improving the health of the dermis were applied to the gums, gingival recession was not only stopped, but gingival recession was reversed. Thus, the oral care compositions described herein provided us with a nonobvious approach to reverse several negative effects of gingival aging including recession.

Figure 1:
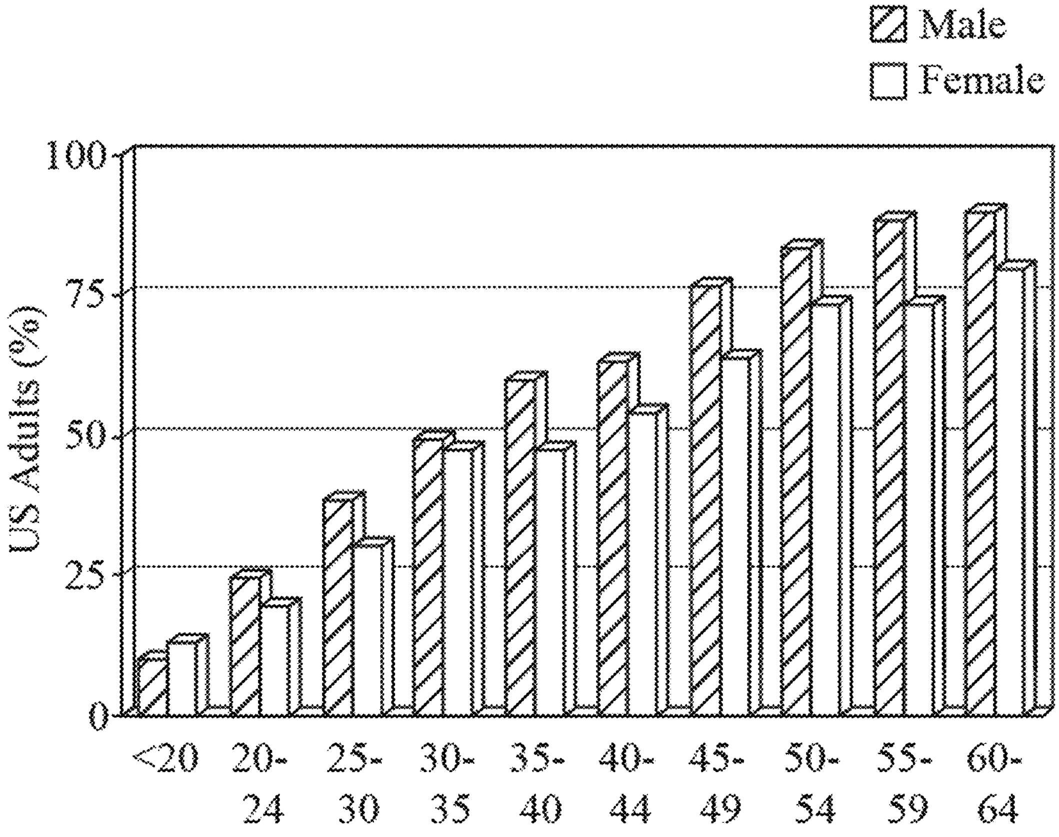
FIG. 1 shows the proportion of the general US population with gum recession according to age.
Figure 2:
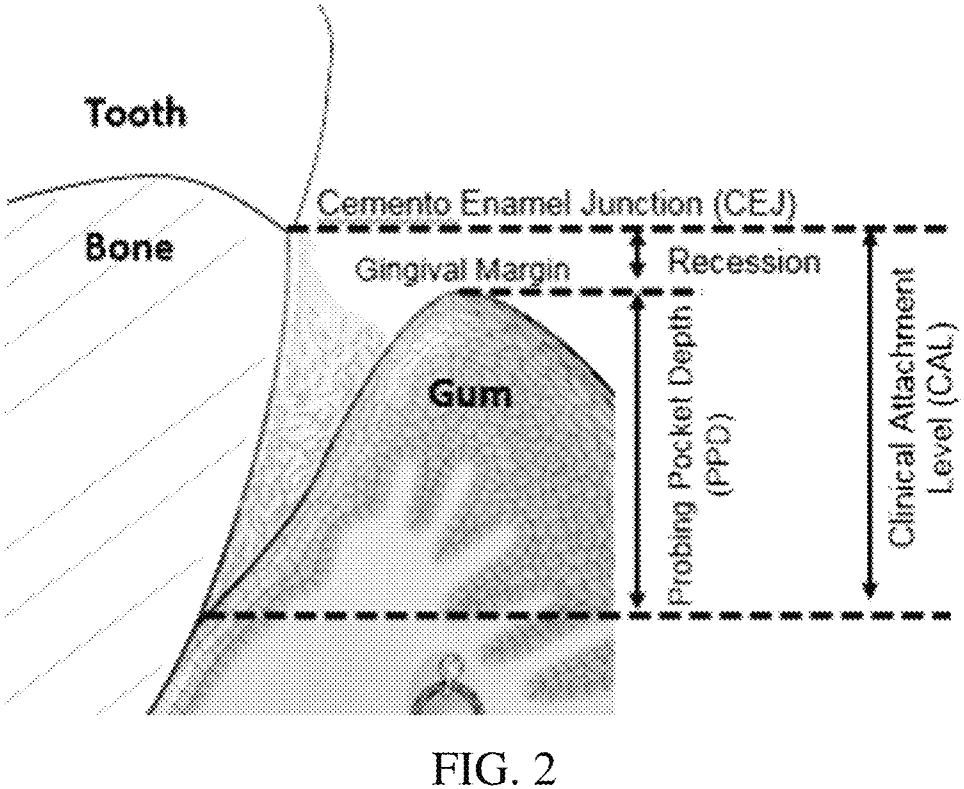
FIG. 2 shows a variety of gum recession measures.

Natural, age-associated gingival recession occurs in nearly all people, as shown in FIG. 1. There are three critical measures for gingival recession, as shown in FIG. 2. Clinical Attachment Level (CAL) is a measurement of gingival recession that depends on the Probing Pocket Depth (PPD). The CAL is a measure of gingival recession that can result from a number of factors including aging and periodontitis. Gingival recession as defined by the relative location of the gingival margin to the Cemento-Enamel Junction (CEJ) is independent of the PPD (Note that the recession metric decreases as the gingival margin recedes below the CEJ such that worsening recession is indicated by a decrease in this metric). This form of gingival recession occurs naturally with age, independent of periodontitis.

Figure 3A:
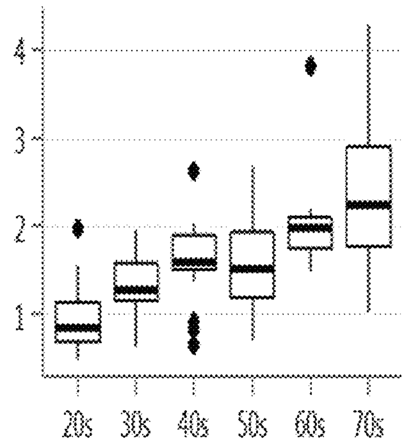
FIG. 3A shows increasing CAL (cor: 0.64, p: 1.7e-11) with respect to age in the gingival aging clinical population.
Figure 3B:
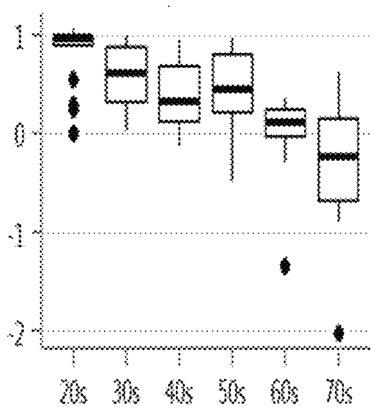
FIG. 3B shows decreasing recession (cor: −0.63, p: 1.8e-11) with respect to age in the gingival aging clinical population. in the gingival aging clinical population.
Figure 4:
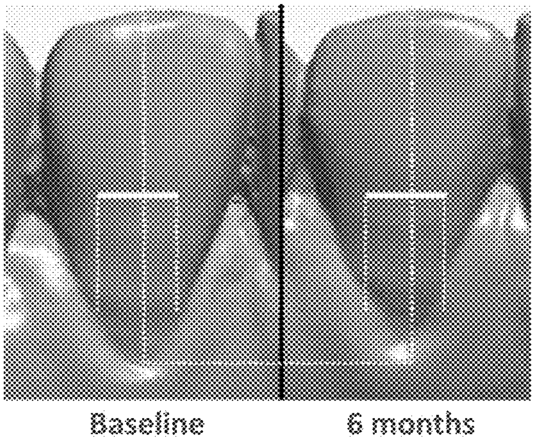
FIG. 4 shows a side by side comparison of (left) a tooth prior to treatment with the disclosed compositions and (right) after six months of treatment with a retinoid compound and a pentapeptide. The upward growth of the gingival margin at the tooth midline and the inward migration is visible after treatment.
Figure 5:
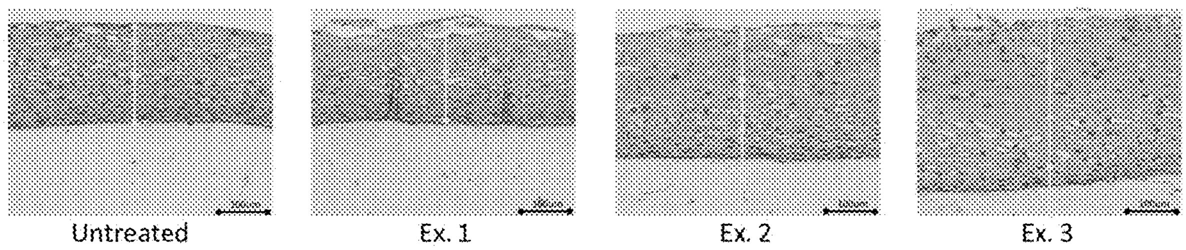
FIG. 5 shows comparison of gingival epithelial layer regrowth upon 48-hour treatments from Inventive Compositions Ex. 2 and Ex. 3 and Comparative Compositions Ex. 1 in an In-vitro 3D full-thickness gingival tissue model assay.

Through natural aging, tissues throughout the human body undergo deleterious physical changes including epithelial tissues such as skin and gingiva. These changes are associated with molecular changes in the expression of important genes and corresponding proteins. To better understand common age-associated molecular changes in two important epithelial tissues, skin and gingiva, we conducted a comparative human clinical study of gene expression change in healthy skin and gingival tissue aging across aged cohorts from 20 years to 70 years in decadal increments. As expected, the studied individuals demonstrated age-associated gingival recession, as shown in FIG. 3.

There are several novel molecular similarities in skin and gingival aging. An analysis of gene expression and a comparison across the aging studies identified similar, statistically significant, decreasing patterns in important collagen genes as a function of age in both skin and gingival tissues. Specifically, we observed age-related decreases in both the major collagen genes, COL1A1 and COL1A2 (shown in Table 1 below).

Collagens are a family of proteins that strengthen and support many tissues in the body, including skin. Type I collagen is the most abundant form of collagen in the human body accounting for 25-35% of all protein in the body, and 75-80% of the protein in skin. The COL1A1 and COL1A2 genes code for proteins that make the type I collagen protein. These proteins cross-link and form the type I collagen fibers that are found in connective tissues throughout the body including skin and the subepithelial connective tissue in gingival (gum) tissue. Importantly, collagen loss in skin is associated with a number of skin aging conditions including laxity, wrinkle formation and dermal thinning. Increasing collagen production is a common target for pharmaceutical agents and cosmetic material compositions for improving skin appearance.

Given the molecular similarities in our comparative aging study, while not wishing to be bound by theory, it was theorized that gingival recession is, at least in part, caused by an age-associate decrease in collagen expression similar to that which occurs during skin aging. Thus, the loss of collagen in subepithelial connective tissue can result in gingival thinning and loss of gingival fibers, both of which contribute to gingival recession. Furthermore, it is believed that chemical compounds that can increase expression of collagen genes in skin may also reverse age-associated gingival recession.

As such, a human clinical protocol for compound screening tested for the expression of collagen genes after the application of materials to the skin. Retinoid compound(s) and/or peptides were shown to be effective in promoting collagen expression.

Based on observations from the comparative skin and gingival aging gene expression studies and the theory that collagen loss contributes to both skin and gingival aging, a human clinical study was conducted to evaluate the effect of the combination of retinol and Pal-KTTKS [SEQ ID NO, 2] when applied topically in a mucoadhesive gel. Treatment with the oral care compositions disclosed increased the amount of collagen in skin when applied to the gums. Importantly, the combination of a retinoid compound and a peptide demonstrated an unexpectedly high improvement relative to the components applied separately.

In total, after six months of treatment, the combination of retinol and Pal-KTTKS [SEQ ID NO. 2] demonstrated statistically significant improvement in gingival recession by multiple measures, Table 2, when compared to the mucoadhesive vehicle alone, which was visibly observable, as shown in MG. 4. Surprisingly, increased gingival resilience to damage and/or improved barrier protection was observed as determined by a reduction in post-brushing abrasion.

While some skin care compositions have been disclosed including retinol, skin care compositions are not expected to be suitable for use in the oral cavity due to the inclusion of compounds not suitable for ingestion. Thus, compositions that are dermatologically acceptable, are not necessarily suitable for use as oral care compositions.

Additionally, in many skin care compositions, retinoids can cause some irritation, which would be unacceptable for oral care compositions. Unexpectedly, retinoids were found to improve gum health with minimal or no irritation.

Unexpectedly, the addition of olive oil, such as olive oil reacted with ethylene glycol, to leave-on oral care compositions including retinoid compound and/or amino acid/peptide led to increased epithelia thickness, greater collagen upregulation, reduction in MMP expression, and reduction in ROS production as shown herein. While not wishing to being bound by theory, it is believed that the use of the olive oil, such as olive oil reacted with ethylene glycol, can enhance the penetration and delivery of the retinoid compound and/or the amino acid/peptide into the epidermal and dermal layers of the gum tissue in the oral cavity. While not wishing to being bound by theory, it is believed that the use of the olive oil, such as olive oil reacted with ethylene glycol, can also act as a source for the building blocks of healthy cell membranes. In total, the addition of olive oil, such as olive oil reacted with ethylene glycol, to a leave-on oral care composition including retinoid compound and/or amino acid/peptide can reduce prevent gingival recession, increase gum resilience, stop gingival recession, reverse gingival recession, promote collagen synthesis, promote fibrillin synthesis, or combinations thereof in an oral cavity of a user of the leave-on oral care composition.

Definitions

By "oral care composition", as used herein, is meant a product that it is retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, denture care products, or denture adhesive products. The oral care composition may also be incorporated onto strips, trays or films for direct application or attachment to oral surfaces.

The term "cone penetration consistency value" as understood herein means the depth, in tenths of a millimeter, that a standard cone will penetrate the sample under fixed conditions of mass, time, and temperature. The cone penetration consistency value is measured according to ASTM method D937-07 first. If the cone penetration consistency value measured according to ASTM method D937-07 is no more than 600, this value is the cone penetration consistency value; if the cone penetration consistency value measured according to ASTM method D937-07 exceeds 600, the cone penetration consistency value is measured according to "Modified version of ASTM method D937-07" specified herein, and this value is the cone penetration consistency value.

The term "delivery carrier" as used herein comprises a material or an appliance that is used to hold the multi-phase oral care composition against the tooth surface. Examples of delivery carriers include strips or dental trays.

The term "strip" as used herein comprises a material 1) whose longest dimension length is generally greater than its width, and 2) whose width is generally greater than its thickness. Strips may be rectangular, arched, curved, semi-circular, have rounded corners, have slits cut into it, have notches cut into it, bent into three dimensional shapes, or combinations thereof. Strips may be solid, semisolid, textured, moldable, flexible, deformable, permanently deformable, or combinations thereof. Strips may be made from plastic sheets including polyethylene, or wax sheets. Examples of strips include a piece of polyethylene about 66 mm long, 15 mm wide and 0.0178 mm thick. Examples of permanently deformable strips include a piece of casting wax sheet about 66 mm long, 15 mm wide, and 0.4 mm thick.

As used herein, the word "or" when used as a connector of two or more elements is meant to include the elements individually and in combination; for example, X or Y, means X or Y or both.

As used herein, the articles "a" and "an" are understood to mean one or more of the material that is claimed or described, for example, "an oral care composition" or "a peptide."

The term "safe and effective amount" as used herein means an amount of a component, high enough to significantly (positively) modify the condition to be treated or to affect the desired whitening result, but low enough to avoid serious side effects (at a reasonable benefit/risk ratio), within the scope of sound medical/dental judgment. The safe and effective amount of a component, will vary with the particular condition being treated, the age and physical condition of the patient being treated, the severity of the condition, the duration of treatment, the nature of concurrent therapy, the specific form employed, and the particular vehicle from which the component is applied.

The term "dispenser", as used herein, means any pump, tube, or container suitable for dispensing oral care compositions.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

The term "teeth", as used herein, refers to natural teeth as well as artificial teeth or dental prosthesis and is construed to comprise one tooth or multiple teeth. The term "tooth surface" as used herein, refers to natural tooth surface(s) as well as artificial tooth surface(s) or dental prosthesis surface(s) accordingly.

The term "orally acceptable carrier" comprises one or more compatible solid or liquid excipients or diluents which are suitable for use in the oral cavity. By "compatible," as used herein, is meant that the components of the composition are capable of being commingled without interaction in a manner which would substantially reduce the composition's stability and/or efficacy.

While specific reference is made to "consumers" or "patients," throughout the specification, these terms are used interchangeably to refer to any user of the multi-phase oral care composition. The consumer or patient can apply the composition to the oral cavity themselves, or have the composition applied to their oral cavity by a third party, such as a dentist, hygienist, orthodontist, or other medical or dental professional.

The term "Gum Care" means those benefits aiming to alleviate one or more symptoms of the earlier stage of gum disease (i.e., gingivitis), which includes: relief of red, swollen, or tender gums; and/or stem gum bleeding.

The term "Gum Health" as used herein refers to inherent or promoted benefits of an oral care composition to provide "Gum Care" benefits that include at least improve gingival and periodontal wound healing, as well as, providing improved gum barrier resilience and strengthening, to mitigate the harmful effects of bacteria as it relates to gum disease, including gingivitis, periodontitis or both.

The term "promoting" as used herein means to promote and/or enhance the Gum Health benefits associated with using the oral care compositions of the present invention in the oral cavity.

The term "substantially free" as used herein refers to the presence of no more than 0.05%, preferably no more than 0.01%, and more preferably no more than 0.001%, of an indicated material in a composition, by total weight of such composition.

The term "essentially free" as used herein means that the indicated material is not deliberately added to the composition, or preferably not present at analytically detectable levels. It is meant to include compositions whereby the indicated material is present only as an impurity of one of the other materials deliberately added.

The term "oral hygiene regimen' or "regimen" can be for the use of two or more separate and distinct treatment steps for oral health. e.g. toothpaste, mouth rinse, floss, toothpicks, spray, water irrigator, massager.

The term "total water content" as used herein means both free water and water that is bound by other ingredients in the oral care composition.

All percentages and ratios used herein after are by weight of total composition (wt %), unless otherwise indicated. All percentages, ratios, and levels of ingredients referred to herein are based on the actual amount of the ingredient, and do not comprise solvents, fillers, or other materials with which the ingredient may be combined as a commercially available product, unless otherwise indicated.

All measurements referred to herein are made at about 23° C. (i.e. room temperature) unless otherwise specified.

All parameters that have a method specified herein are measured using the method specified herein, unless otherwise specified.

The oral care compositions, as described herein, comprise retinoid compound, amino acid peptide, and/or olive oil. Additionally, the oral care compositions can comprise other optional ingredients, as described below. The section headers below are provided for convenience only. In some cases, a compound can fall within one or more sections. For example, stannous fluoride can be a tin compound and/or a fluoride compound.

Retinoid Compound

The leave-on oral care compositions comprises one or more retinoid compounds. As used herein, "retinoid compound" includes all natural and/or synthetic analogs of Vitamin A or retinol-like compounds that possess the biological activity of Vitamin A in the skin as well as the geometric isomers and stereoisomers of these compounds. The retinoid compound can, for example, be retinol, retinyl esters (e.g., C—C alkyl esters of retinol, including retinyl palmitate, retinyl acetate, retinyl propionate), retinal, and/or retinoic acid (including all-trans retinoic acid and/or 13-cis-retinoic acid). In some embodiments, retinoids other than retinoic acid are used. These compounds are available in the art and are commercially available from several sources, e.g., Sigma Chemical Company (St. Louis, Mo.), and Boehringer Mannheim (Indianapolis, Ind.). Other suitable retinoids are tocopheryl-retinoate, tocopherol ester of cis- or trans-retinoic acid, adapalene (6-3-(1-adamantyl)-4-methoxyphenyl-2-naphthoic acid), and tazarotene (ethyl 6-2-(4.4-dimethylthiochroman-6-yl)-ethynylnicotinate). Desirable retinoids include retinol, retinoic acid, retinyl palmitate, retinyl acetate, retinyl propionate, retinal, and combinations thereof.

The retinoid compound may be included as the substantially pure material, or as an extract obtained by suitable physical and/or chemical isolation from natural (e.g., plant) sources. The retinoid compound can be substantially pure, or essentially pure. The compositions of this invention may contain a safe and effective amount of the retinoid compound, such that the oral care composition is safe and effective for regulating or improving the condition of keratinous tissues and accidental ingestion since applied to the oral cavity.

The retinoid compound can comprise retinol, retinyl ester, retinal, retinoic acid, tocopheryl-retinoate, tocopherol ester of cis- or trans-retinoic acid, isotretinoin, alitretinoin, etretinate, acitretin, adapalene, bexarotene, tazarotene, or combinations thereof. The retinoid compound can be pharmaceutical grade, USP, or the like grade, due to use in the oral cavity. The retinoid compound and/or the retinol can have a purity of at least about 95%, at least about 97%, at least about 99%, at least about 99.5%, or at least about 99.9%. The oral care composition can comprise from about 0.0001% to about 10%, from about 0.01% to about 5%, or from about 0.01% to about 2%, by weight of the composition, of retinoid compound. The oral care composition can comprise from about 1 ppm to about 10,000 ppm, from about 500 ppm to about 5000 ppm, from about 750 ppm to about 5000 ppm, from about 1000 ppm to about 2500 ppm, about 1500 ppm, or about 2250 ppm of retinoid compound. Amounts of retinoid compound that are greater than about 5000 ppm are thought to lead to toxicity concerns for formulating with oral care compositions, which would not be present in skin care compositions.

The retinoid compound can comprise retinol comprising cis- and/or trans-alkene functional groups. The retinol can comprise at least about 80%, at least about 90%, at least about 95%, and/or at least about 99% of trans-alkene functional groups.

The retinoid compound can also comprise surfactant, such as anionic surfactant, cationic surfactant, and/or nonionic surfactant, which can improve gum barrier permeability. Suitable surfactants can include polysorbate.

Amino Acid

The leave-on oral care composition can comprise amino acid. The amino acid can comprise one or more amino acids, peptide, and/or polypeptide, as described herein. Unexpectedly, it has been found that the combination of retinoid compound and amino acid can improve the gum health of a user.

Amino acids, as in Formula I, are organic compounds that contain an amine functional group, a carboxyl functional group, and a side chain (R in Formula I) specific to each amino acid. Suitable amino acids include, for example, amino acids with a positive or negative side chain, amino acids with an acidic or basic side chain, amino acids with polar uncharged side chains, amino acids with hydrophobic side chains, and/or combinations thereof. Suitable amino acids also include, for example, arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, citrulline, ornithine, creatine, diaminobutonic acid, diaminoproprionic acid, salts thereof, and/or combinations thereof.

Suitable amino acids include the compounds described by Formula I, either naturally occurring or synthetically derived. The amino acid can be zwitterionic, neutral, positively charged, or negatively charged based on the R group and the environment. The charge of the amino acid would be well known to one of ordinary skill in the art.

Formula I

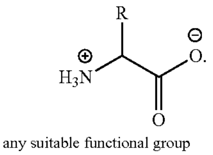

Amino Acid. R is any suitable functional group

Suitable amino acids include one or more basic amino acids, one or more acidic amino acids, one or more neutral amino acids, or combinations thereof.

The oral care composition can comprise from about 0.01% to about 20%, from about 0.1% to about 10%, from about 0.5% to about 6%, or from about 1% to about 10% of amino acid, by weight of the oral care composition.

The term "neutral amino acids" as used herein include not only naturally occurring neutral amino acids, such as alanine, asparagine, cysteine, glutamine, glycine, isoleucine, leucine, methionine, phenylalanine, proline, serine, threonine, tryptophan, tyrosine, valine, but also biologically acceptable amino acid which has an isoelectric point in range of pH 5.0 to 7.0. The biologically preferred acceptable neutral amino acid has a single amino group and carboxyl group in the molecule or a functional derivative hereof, such as functional derivatives having an altered side chain albeit similar or substantially similar physio chemical properties. In a further embodiment the amino acid would be at minimum partially water soluble and provide a pH of less than 7 in an aqueous solution of 1 g/1000 ml at 25° C.

Accordingly, neutral amino acids suitable for use in the invention include, but are not limited to, alanine, aminobutyrate, asparagine, cysteine, cystine, glutamine, glycine, hydroxyproline, isoleucine, leucine, methionine, phenylalanine, proline, serine, taurine, threonine, tryptophan, tyrosine, valine, salts thereof, or mixtures thereof. Preferably, neutral amino acids used in the composition of the present invention may include asparagine, glutamine, glycine, salts thereof, or mixtures thereof. The neutral amino acids may have an isoelectric point of 5.0, or 5.1, or 5.2, or 5.3, or 5.4, or 5.5, or 5.6, or 5.7, or 5.8, or 5.9, or 6.0, or 6.1, or 6.2, or 6.3, or 6.4, or 6.5, or 6.6, or 6.7, or 6.8, or 6.9, or 7.0, in an aqueous solution at 25° C. Preferably, the neutral amino acid is selected from proline, glutamine, or glycine, more preferably in its free form (i.e. uncomplexed). If the neutral amino acid is in its salt form, suitable salts include salts known in the art to be pharmaceutically acceptable salts considered to be physiologically acceptable in the amounts and concentrations provided. Preferably the neutral amino acid is present in the amount of from about 0.0001% to about 10%, preferably from about 0.05% to about 5%, preferably from about 0.1% to about 3%, preferably from about 0.5% to about 3%, preferably from about 1% to about 3%, by weight of the composition. In one aspect, the neutral amino acid is glutamine (or salt thereof). In another aspect, the neutral amino acid is proline (or salt thereof). In yet another aspect, the neutral amino acid is glycine (or salt thereof).

It has been surprisingly discovered that, the use of neutral amino acid increases the collagen synthesis of gingival fibroblasts within a topical leave on application.

The oral care composition can comprise from about 0.0001% to about 20%, from about 0.1% to about 10%, from about 0.5% to about 6%, or from about 1% to about 10% of neutral amino acid, by weight of the oral care composition.

Peptide

The oral care composition can also comprise a peptide. A peptide is a linear organic polymer consisting of a number of amino-acid residues bonded together in a chain, forming part of (or the whole of) a protein molecule. The peptide can comprise from two amino acids to ten amino acids, from two amino acids to five amino acids, or from four amino acids to six amino acids.

Peptides, including but not limited to, di-, tri-, tetra-, and pentapeptides and derivatives thereof, may be included in the compositions of the present invention in amounts that are safe and effective, including safe and effective for ingestion. As used herein, "peptides' refers to both the naturally occurring peptides and synthesized peptides. Also, useful herein are naturally occurring and commercially available compositions that contain peptides.

Suitable dipeptides for use herein include, for example, Carnosine (beta-ala-his). Suitable tripeptides for use herein include, for example, gly-his-lys, arg-lys-arg, and/or his-gly-gly. Suitable tripeptide derivatives include palmitoyl-gly-his-lys, which may be purchased as Biopeptide CL™ (100 ppm of palmitoyl-gly his-lys commercially available from Sederma, France); Peptide CK (arg-lys-arg); Peptide CK(ac-arg-lys-arg-$NH_2$); and a copper derivative of his-gly-gly sold commercially as Iamin, from Sigma (St. Louis, Mo.). Suitable tetrapeptides for use herein include, for example, Peptide E, arg-ser-arg-lys (SEQ ID NO. 1).

Suitable pentapeptides for use herein include lys-thr-thr-lys-ser (SEQ ID NO. 2). A preferred commercially available pentapeptide derivative composition is Matrixyl™, which contains 100 ppm palmitoyl-lys-thr-thr-lys-ser, (SEQ ID NO. 2, commercially available from Sederma France).

The peptide can comprise palmitoyl-lys-thr-thr-lys-ser (SEQ ID NO. 2), palmitoyl-gly-his-lys, beta-ala-his, their derivatives, and/or combinations thereof. In some embodiments, the peptide comprises palmitoyl-lys-thr-thr-lys-ser (SEQ ID NO. 2), palmitoyl-gly-his-lys, their derivatives, or combinations thereof. In other embodiments, the peptide comprises palmitoyl-lys-thr-thr-lys-ser (pal-KTTKS, SEQ ID NO. 2) and/or derivatives thereof. Other suitable peptides include gly-his-ly (GHK), gly-glu-lys-gly (GEKG, SEQ ID NO. 3), or combinations thereof.

Olive Oil

The leave-on oral care composition comprises olive oil. Olive oil can be provided by pressing olives, such as into an olive paste, and extracting the oil and/or a suitable synthetic analog incorporating one or more of the disclosed ingredients. Olive oil can include olive oil triglycerides, olive oil fatty acid, glycerol, phosphatide, sterol, whole pieces of olive, and/or combinations thereof. Commercial olive oil is a mixture of olive oil triglycerides, olive oil fatty acid, glycerol, phosphatide, sterol, and whole pieces of olive.

Olive oil can include olive oil fatty acid, which can be found in a "free" or unbound form, as a carboxylate salt with a suitable cation, and/or incorporated as an ester in an olive oil triglyceride, as further discussed below. The olive oil fatty acid can include saturated fatty acid, monounsaturated (cis and/or trans configuration) fatty acid, and/or polyunsaturated (cis and/or trans configurations) fatty acid.

The olive oil fatty acid can include a single carboxylic acid functional group attached to an alkyl functional group or a fatty functional group. The alkyl functional group can be saturated, monounsaturated, and/or polyunsaturated. The alkene functional group present in the unsaturated fatty acid can be in the cis or trans configuration. In total, and inclusive of the carbon atom present in the carboxylic acid functional group, the olive oil fatty acid can include from about 5 to about 50, from about 10 to about 30, or from about 15 to about 20 carbon atoms. Specific examples of suitable olive oil fatty acids include oleic acid, linoleic acid, palmitic acid, stearic acid, linolenic acid, or combinations thereof.

Olive oil triglyceride comprises molecules derived from the natural esterification of three olive oil fatty acids with a glycerol molecule. The three olive oil fatty acid molecules that make the fatty acid portion of the olive oil triglyceride can be independently selected from the disclosed olive oil fatty acids. The olive oil triglyceride can include three of the same olive oil fatty acids, two of the same olive oil fatty acids, or each olive oil fatty acid can be unique.

The olive oil can also include olive oil diglyceride and/or olive oil monoglyceride.

The olive oil can be provided in any suitable commercial grade including virgin olive oil, extra virgin olive oil, lampante virgin olive oil, refined olive oil, crude olive pomace oil, or combination of these grades of olive oil.

The olive oil can also be further processed through a direct oxidation reaction with ethylene oxide, which can be known as a PEGylation reaction, such as described in Sugar, M.; Clausen, A.; Ruppert, S. Cosmetic Cleansing Compositions Containing Olive Oil-PEG-7-Carboxylate and/or US Patent Application Publication No. 2004/0265264. The reaction of olive oil with ethylene oxide can result in the insertion of repeating units of ethylene glycol into each of the components of olive oil, as described herein. The PEGylated olive oil can comprise PEGylated olive oil triglyceride, PEGylated olive oil diglyceride, PEGylated olive oil monoglyceride, PEGylated olive oil fatty acid, or combinations thereof. The PEGylated olive oil can comprise PEGylated olive oil carboxylic acid, a salt thereof, such as a sodium or potassium salt, or a mixture thereof. The term "PEGylated" indicates that one or more units of ethylene glycol repeating units into the referenced compound. For example, PEGylated olive oil triglyceride indicated that one or more ethylene glycol repeating units have been incorporated between each of the olive oil fatty acid molecules and the glycerol moiety of the glyceride (i.e. three separate repeating sections of ethylene glycol molecules). PEGylated olive oil fatty acid includes free olive oil fatty molecules with one or more ethylene glycol repeating units incorporated.

The PEGylated olive oil carboxylic acid can comprise sodium PEG-n olive oil carboxylate and n is a number from about 4 to about 20, from about 5 to about 10, or from about 6 to about 9. The PEG olive oil carboxylic acid can comprise sodium PEG-7 olive oil carboxylate. The number n represents the number of stoichiometric equivalents of ethylene oxide that were added to one stoichiometric equivalent of an olive oil compound.

Other components of PEGylated olive oil include Glycereth-7, Lauramidopropyl betaine, Myristamidopropyl betaine, Glycereth-8 monolaurate, Laureth-10, Laureth-8 carboxylate, Sodium laureth-8 carboxylate, Trideceth-10, Trideceth-8 carboxylate, Sodium trideceth-8 carboxylate, Glycereth-7 monooleate, Glycereth-8 monopalmitate, Glycereth-8 monostearate, Glycereth-6 dilaurate, Glycereth-6 monolaurate/monooleate, Glycereth-6 monolaurate/monopalmitate, Glycereth-6 monooleate/monolinoleate, Glycereth-6 dioleate, Glycereth-6 monopalmitate/monooleate, or combinations thereof.

Suitable sources of olive oil, such as PEGylated olive oil, include modified olive oil from Hallstar, such as olive oil derived emulsifiers under the Olivem® brand name. A suitable surfactant derived from olive oil includes Olivem® 400.

Unexpectedly, the addition of olive oil, such as olive oil reacted with ethylene glycol, to leave-on oral care compositions including retinoid compound and/or amino acid/peptide led to increased epithelia thickness, greater collagen upregulation, reduction in MMP expression, and reduction in ROS production as shown herein. While not wishing to being bound by theory, it is believed that the use of the olive oil, such as olive oil reacted with ethylene glycol, can enhance the penetration and delivery of the retinoid compound and/or the amino acid/peptide into the epidermal and dermal layers of the gum tissue in the oral cavity. While not wishing to being bound by theory, it is believed that the use of the olive oil, such as olive oil reacted with ethylene glycol, can also act as a source for the building blocks of healthy cell membranes. In total, the addition of olive oil, such as olive oil reacted with ethylene glycol, to a leave-on oral care composition including retinoid compound and/or amino acid/peptide can reduce prevent gingival recession, increase gum resilience, stop gingival recession, reverse gingival recession, promote collagen synthesis, promote fibrillin synthesis, or combinations thereof in an oral cavity of a user of the leave-on oral care composition.

The leave-on oral care composition can comprise from about 0.001% to about 10%, from about 0.01% to about 5%, or from about 0.01% to about 2%, by weight of the oral care composition, of the olive oil.

Metal

The oral care composition of the present invention can comprise metal. The metal can be provided by a metal ion source. The metal ion source can comprise tin, zinc, copper, or combinations thereof. The metal can provide a gum health benefit. The oral care composition can comprise from about 0.01% to about 5%, from about 0.1% to about 10%, from about 0.001% to about 1%, from about 0.2% to about 1%, from about 0.5% to about 1.5%, or from about 0.3% to about 0.6%, by weight of the oral care composition, of the metal and/or metal ion source.

The metal of the present invention comprise tin, which can be provided by a tin ion source. The tin ion source can be any suitable compound that can provide tin ions in an oral care composition and/or deliver tin ions to the oral cavity when the dentifrice composition is applied to the oral cavity. The tin ion source can comprise one or more tin containing compounds, such as stannous fluoride, stannous chloride, stannous bromide, stannous iodide, stannous oxide, stannous sulfate, stannous sulfide, stannic fluoride, stannic chloride, stannic bromide, stannic iodide, stannic sulfide, and/or mixtures thereof. Preferably, the tin ion source can comprise stannous fluoride, stannous chloride, and/or mixture thereof.

The oral care composition can comprise from about 0.01% to about 5%, from about 0.1% to about 10%, from about 0.001% to about 1%, from about 0.2% to about 1%, from about 0.5% to about 1.5%, or from about 0.3% to about 0.6%, by weight of the oral care composition, of the tin and/or tin ion source.

The metal of the present invention comprise zinc, which can be provided by a zinc ion source. The zinc ion source can comprise one or more zinc containing compounds, such as zinc fluoride, zinc lactate, zinc oxide, zinc phosphate, zinc chloride, zinc acetate, zinc hexafluorozirconate, zinc sulfate, zinc tartrate, zinc gluconate, zinc citrate, zinc malate, zinc glycinate, zinc pyrophosphate, zinc metaphosphate, zinc oxalate, and/or zinc carbonate.

The oral care composition can comprise from about 0.01% to about 5%, from about 0.1% to about 10%, from about 0.001% to about 1%, from about 0.2% to about 1%, from about 0.5% to about 1.5%, or from about 0.3% to about 0.6%, by weight of the oral care composition, of the zinc and/or zinc ion source.

Gum Strengthening Polyol

The oral care composition of the present invention can comprise a gum-strengthening polyol. The applicant has discovered that gum-strengthening polyols have been shown to additionally strengthen the barrier function of epithelial cells in the oral cavity.

The term "gum-strengthening polyol" can be a sugar alcohol, a disaccharide, a polysaccharide, and preferably a non-reducing sugar. Sugar alcohols are a class of polyols that can be obtained through the hydrogenation of sugar compounds with the formula $(CHOH)_nH_2$, where n is seven or more, such as isomalt, maltitol, lactitol, maltotriitol, maltotetraitol, polyglycitol, or combinations thereof. Preferably, n is from about 7 to about 12. Even more preferably, the gum-strengthening polyol is isomalt, maltitol, lactitol, or combinations thereof.

Non-reducing sugars are a class of saccharides that do not generate any compounds containing an aldehyde or ketone functional group. Non-reducing sugars are stable in water and do not react with weak oxidizing agents to produce sugar alcohols. Non-reducing sugars cannot donate electrons to other molecules, and is typically a di, tri, tetra, penta saccharide, such as sucrose, trehalose, raffinose, stachyose, verbascose, or combinations thereof. Preferably, the gum-strengthening polyol is trehalose. The gum barrier properties can be obtained from a combination mixture of polyols whereby all have seven or more hydroxyl functional groups.

The oral care composition can comprise from about 0.0001% to about 20%, from about 0.1% to about 18%, from about 0.2% to about 15%, from about 0.5% to about 15%, or from about 1% to about 12%, by weight of the oral care composition, of a gum-strengthening polyol.

The gum-strengthening property can be characterized by Barrier Protection ability as described herein below. For example, a polyol exhibiting the Barrier Protection of more than 10% at concentration of 0.5 wt % can be qualified as a gum-strengthening polyol. In other examples, the gum-strengthening polyol can include polyols having five or more hydroxyl functional groups as long which can provide above-mentioned Barrier Protection ability.

Allantoin

The oral care composition can comprise from about 0.01% to about 5%, by weight of the composition, of allantoin. Allantoin, also called 5-ureidohydantoin or glyoxyldiureide, is an oxidation product of uric acid. Allantoin helps to heal wounds and skin irritations and stimulates the growth of healthy tissue. In some examples, the allantoin can be present in the amount of from about 0.02% to about 4%, or from about 0.05% to about 3%, by weight of the composition. For example, the allantoin can be present in the amount of about 0.05%, or about 0.1%, or about 0.2%, or about 0.3%, or about 0.4%, or about 0.5%, or about 0.6%, or about 0.8%, or about 0.9%, or about 1%, by weight of the composition. Allantoin can help to improve or increase the wound healing benefit for the hyaluronic acid-containing composition.

Hydroxy Acid

The oral care compositions may comprise a hydroxy acid. The hydroxy acids can be alpha-hydroxy or beta-hydroxy acids. Examples of hydroxy acids for use in the compositions of the present invention include salicylic acid, lactic acid, glycolic acid, acetylsalicylic acid, and other salicylic acid derivatives. In some embodiments, salicylic acid and the synthetic and naturally occurring derivatives of salicylic acid can be used in the compositions and methods of the present invention. The hydroxy acid can comprise a compound from Formula II.

Formula II

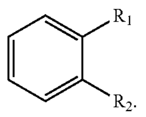

wherein:

$R_1$ is COOR, or —$(CH_2)_n$—OX

R is H, or alkyl (e.g., with one to twenty carbons);

n is an integer of about 1 to about 20;

X is H, or 1 to 6 sugar residues (e.g., hexoses or pentoses);

$R_2$ is COOR, —$(CH_2)_n$—OX, OCO-alkyl ($C_1$-$C_{20}$), or OY; and

Y is H, alkyl ($C_1$-$C_{20}$), or 1 to 6 sugar residues (e.g., hexoses or pentoses).

In general, the alkyl groups employed in these hydroxy acid compounds have about one to twenty carbon atoms, although in some embodiments lower alkyl groups are used, for example, alkyl groups with about one to eight carbon atoms. Alkyl groups with even lower numbers of carbon atoms can also be used, for example, alkyl groups with one to six, or one to three carbon atoms.

In some embodiments, salicylic acid is employed in the compositions of the invention. Salicylic acid is a compound of Formula II wherein $R_1$ is COOH and $R_2$ is OH. In other embodiments, acetylsalicylic acid is employed in the compositions of the invention. Acetylsalicylic acid is a compound of Formula I wherein $R_1$ is COOH and $R_2$ is $OCOCH_3$.

When present in the compositions of the present invention, the hydroxy acid can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of acetylsalicylic acid or salicylic acid that range from about $10^{-4}$ M to about $10^{-6}$ M are effective for increasing cell proliferation and stimulating the production of collagen in mammalian keratinous tissue.

Alternatively, the oral care compositions can be substantially free of, essentially free of, or free of hydroxy acid. The oral care compositions can comprise less than about 0.001% of hydroxy acid.

Gibberellic Acid

The oral care compositions of the present invention can comprise gibberellic acid. Gibberellic acid comprises a class of compounds that is also referred to as gibberellins. Gibberellins are plant hormones that affect a wide variety of processes throughout the life cycle of plants, including seed germination, stem elongation, flower induction, another development, and seed and pericarp growth. Gibberellins are tetracyclic diterpenoid acids found in fungi and higher plants having the ent-gibberellane ring system.

When present in the compositions of the present invention, gibberellic acids or their derivatives can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of an active gibberellic acid ranging from about $10^{-4}$ M to about $10^{-6}$ M are effective for increasing cell proliferation and stimulating the production of collagen in mammalian keratinous tissue.

Alternatively, the oral care compositions can be substantially free of, essentially free of, or free of gibberellic acid. The oral care compositions can comprise less than about 0.001% of gibberellic acid.

Jasmonic Acid

The oral care compositions of the present invention can comprise jasmonic acid compounds. Jasmonic acid compounds employed in the invention include jasmonic acid and jasmonic acid derivatives available to one of skill in the art. Such compounds include jasmonic acid, methyl jasmonate and their isomers. In the present invention jasmonic acid and jasmonic acid derivatives used can include synthetic and natural stereoisomers of jasmonic acid, dihydrojasmonic acid, hydroxy jasmonic acid and dihydro-hydroxy jasmonic acid.

When present in the compositions of the present invention, jasmonic acids or jasmonic acid derivatives can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of jasmonic acid ranging from about $10^{-4}$ M to about $10^{-6}$ M are effective for increasing cell proliferation and stimulating the production of collagen in mammalian keratinous tissue.

Alternatively, the oral care compositions can be substantially free of, essentially free of, or free of jasmonic acid compound. The oral care compositions can comprise less than about 0.001% of jasmonic acid compound.

Zeatin Compounds

The oral care compositions of the present invention can comprise zeatin compounds. Zeatin compounds employed in the invention include the cis and trans isomers of zeatin and the cis and trans isomers of zeatin derivatives available to one of skill in the art. Such zeatin compounds and zeatin derivatives can be natural and synthetic derivatives of the compounds provided by Formula III below.

Formula III

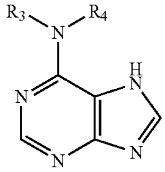

wherein $R_3$ is H, 3-hydroxymethyl-3-methylallyl, alkyl, $—(CH_2)_n—CH_3$, or OZ;

Z is H, 1 to 6 sugar residues (e.g., hexoses or pentoses), or $—(CH_2)_n$-furan;

$R_4$ is H, 3-hydroxymethyl-3-methylallyl, alkyl, —(CH)n-C, or OZ; and n is an integer of from about 1 to about 20.

In some embodiments, zeatin is employed in the compositions of the invention. Zeatin can be a compound of Formula III wherein $R_3$ is 3-hydroxymethyl-3-methylallyl, and $R_4$ is H.

When present in the compositions of the present invention, zeatin or its derivatives can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of zeatin ranging from about 10 $M^{-4}$ to about $10^{-6}$ M are effective for increasing cell proliferation and stimulating the production of collagen in mammalian keratinous tissue.

Alternatively, the oral care compositions can be substantially free of, essentially free of, or free of zeatin compound. The oral care compositions can comprise less than about 0.001% of zeatin compound.

The oral care composition can comprise from about 0.0001% to about 10%, from about 0.01% to about 5%, from about 0.001% to about 5%, from about 0.01% to about 2%, or from about 0.0001% to about 1%, by weight of the composition of peptide. The oral care composition can comprise from about 1 ppm to about 1000 ppm, from about 1 ppm to about 100 ppm, from about 3 ppm to about 50 ppm, or from about 1 ppm to about 10000 ppm, by weight of the oral care composition, of peptide. Amounts of peptide that are greater than about 10000 ppm are thought to lead to toxicity concerns for formulating with oral care compositions, which would not be present in skin care compositions.

Mucoadhesive Polymer

The oral care composition of the present invention can comprise a mucoadhesive polymer. The mucoadhesive polymer can provide increased retention time on a surface of the oral cavity, such as the gums. Suitable mucoadhesive polymers include polyacrylic acid, natural gum, linear sulfated polysaccharide, chitosan, alginate, anionic cellulose, non-ionic cellulose derivative, poly-vinyl based homopolymers, poly-vinyl based copolymer or high molecular weight polyethylene oxides (PEO) homopolymers, polypropylene oxide co-polymer, polymers comprising at least a polycarboxylated ethylene backbone, hyaluronic acid or salt thereof and/or combinations thereof.

Polyacrylic acid (PAA) polymer is a generic term for the synthetic high molecular weight polymers of acrylic acid. These may be homopolymers of acrylic acid, crosslinked with an allyl ether pentaerythritol, allyl ether of sucrose or allyl ether of propylene. And, in a water solution at neutral pH, PAA is an anionic polymer, i.e. many of the side chains of PAA will lose their protons and acquire a negative charge. This makes PAAs polyelectrolytes, with the ability to absorb and retain water and swell to many times their original volume. Polyacrylic acid is also called carbomer as tradename. For example, Carbopol®-type polymers, such as Carbopol®, Pemulen® and Noveon®, are polymers of acrylic acid, crosslinked with polyalkenyl ethers or divinyl glycol. Carbomer commercial codes, e.g. 940™, indicate the molecular weight and the specific components of the polymer.

Preferably, a natural gum is selected from the group consisting of gum karaya, gum arabic (also known as acacia gum), gum tragacanth, xanthan gum, alginates, chitosan and combination thereof. More preferably, the natural gum is xanthan gum. Xanthan gum is a polysaccharide secreted by the bacterium *Xanthomonas camestris*. Generally, xanthan gum is composed of a penta-saccharide repeat units, comprising glucose, mannose, and glucuronic acid in a molar ratio of 2:2:1, respectively. The chemical formula (of the monomer) is $C_{35}H_{49}O_{29}$. In one example, the xanthan gum is from CP Kelco Inc (Okmulgee, US).

Preferably, the hyaluronic acid or a salt thereof is a viscoelastic linear polysaccharide of molecular weight range (1000 to 10,000,000 Da). It is naturally present in the connective tissue of vertebrates, a polymer of glucuronic acid and n-acetyglucosylamine, and is a member of glucosamine family with a high molecular weight. Hyaluronic acid (Hyaluronan) is an indispensable component of intact, healthy gingiva, and oral mucosal tissue. It has many properties that make it a potentially ideal molecule for assisting wound healing by inducing early granulation tissue formation, inhibiting inflammation, promoting epithelial turnover and also connective tissue angiogenesis. Preferably, the hyaluronic acid used in the present invention has a weight average molecular weight (M.W.) of from about 900,000 Daltons to about 5,000,000 Daltons, preferably from about 900,000 Daltons to about 3,000,000 Daltons; more preferably from about 900,000 Daltons to about 2,000,000 Daltons. The molecular weight of the hyaluronic acid can be measured using Gel Electrophoresis method.

Preferably, the linear sulfated polysaccharide is a carrageenan. Examples of carrageenan include Kappa-carrageenan, Iota-carrageenan, Lambda-carrageenan, and combinations thereof. In one example, the linear sulfated polysaccharide is Iota-carrageenan.

Preferably, the anionic cellulose is a carboxymethyl cellulose ("CMC"). In one example, the CMC is prepared from cellulose by treatment with alkali and monochloroacetic acid or its sodium salt. Different varieties are commercially characterized by viscosity. One commercially available example is Aqualon™ branded CMC from Ashland Special Ingredients (e.g., Aqualon™ 7H3SF; Aqualon™ 9M3SF Aqualon™ TM9A; Aqualon™ TM12A).

Preferably, the nonionic cellulose or derivative thereof has a weight average molecular weight range of about 50,000 Daltons to about 1,300,000 Daltons, and preferably an average degree of polymerization from 300 to 4,800. More preferably, the nonionic cellulose or derivative thereof is hydroxyethyl cellulose ("HEC"). In other examples, the nonionic cellulose may be hydroxypropyl cellulose or hydroxymethyl cellulose.

Preferably the non-ionic synthetic polymers, including but limited to include poly-vinyl based homopolymers, polyvinyl pyrolidone (PVP), polyvinyl acetate (PVA) or poly-vinyl based copolymer e.g. poly pyrolidone-co-vinyl acetate (PVP/VA) or high molecular weight polyethylene oxides (PEO) homopolymers (Polyox WSR family) or polypropylene oxide co-polymer (Poloxamers).

Preferably, the polymer comprising at least a polycarboxylated ethylene backbone is selected from the group consisting of co-polymers of maleic anhydride with methyl vinyl ether having a weight average molecular weight of from about 30,000 Daltons to about 1,000,000 Daltons; and co-polymers of maleic acid and acrylic acid or methacrylic.

In an example, the GANTREZ™ series of polymers are co-polymers of maleic anhydride with methyl vinyl ether having a weight average molecular weight (M.W.) of about 30,000 Daltons to about 1,000,000 Daltons. These co-polymers are available for example as GANTREZ™ AN139 (M.W. 500,000 Daltons), AN119 (M.W. 250,000 Daltons) and S-97 Pharmaceutical Grade (M.W. 70,000 Daltons), from Ashland Chemicals (Kentucky, USA).

In another example, the ACUSOL™ and the SOKALAN series of polymers include homopolymers of acrylic acid and copolymers of maleic acid and acrylic acid or methacrylic. Examples are 0:1000 to 1000:0 copolymers of maleic acid with acrylic acid having a weight average molecular weight (M.W.) of about 2,000 to about 1,000,000 Daltons. These copolymers are commercially available as ACUSOL™ 445 and 445N, ACUSOL™ 531, ACUSOL™ 463, ACUSOL™ 448, ACUSOL™ 460, ACUSOL™ 465, ACUSOL™ 497, ACUSOL™ 490 from Dow Chemicals (Michigan, USA) and as Sokalan® CP 5, Sokalan® CP 7, Sokalan® CP 45, and Sokalan® CP 12 S from BASF (New Jersey, USA).

The use of thiolated mucoadhesive polymer, whereby free thiol groups in the polymer skeleton can help in the formation of the disulfide bonds with that of the cysteine-rich sub-domains present in the mucin which can substantially improve the mucoadhesive properties of the polymers. Thiolated polymers, including but not limited to, chitosan-iminothiolane, poly(acrylicacid)-cystseine, poly(acrylic acid)-homocysteine, chitosan-thioglycolicacid, chitosan-thioethylamidin, alginate-cysteine, sodium carboxymethylcellulose-cysteine.

The oral care composition can comprise from about 0.01% to about 20%, from about 0.01% to about 10%, from about 0.1 to about 8%, or from about 0.001% to about 25%, by weight of the composition of the mucoadhesive polymer.

Additionally or alternatively, the oral care composition can comprise polyacrylic acid an additional polymer, such as natural gum, linear sulfated polysaccharide, anionic cellulose, nonionic cellulose derivative, poly-vinyl based homopolymers, poly-vinyl based copolymer or high molecular weight polyethylene oxides (PEO) homopolymers, polypropylene oxide co-polymer, polymers comprising at least a polycarboxylated ethylene backbone, and/or combinations thereof, in a ratio that provides an optimal viscosity, good adhesion, and retention efficacy that provides a better sensory benefit.

Additionally, the oral care composition can comprise, from about 0.01% to about 5%, from about 0.1% to about 1%, from about 0.01% to about 2%, from about 0.2% to about 0.8%, or from about 0.01% to about 1%, by weight of the composition, of hyaluronic acid, a salt of hyaluronic acid, or combinations thereof.

The oral care composition can comprise from about 0.01% to about 5%, from about 0.5% to about 10%, or from about 0.1% to about 5%, by weight of the oral care composition, of polyacrylic acid. The oral care composition can comprise from about 0.1% to about 10%, from about 0.5% to about 6%, from about 1% to about 5%, from about 1.3% to about 2.6%, by weight of the composition, of the additional polymer. The additional polymer can comprise natural gum, linear sulfated polysaccharide, anionic cellulose, chitosan, alginate, nonionic cellulose derivative, polyvinyl pyrrolidine, hyaluronic acid or salt thereof, or polymers comprising at least a polycarboxylated ethylene backbone, and combinations thereof.

In some examples, the ratio of the polyacrylic acid and the additional polymer in the oral care composition of the present invention can be from about 5:1 to about 1:5, preferably from about 3:1 to about 1:3. For example, the ratio of the polyacrylic acid and the additional polymer in the present oral care composition, by weight, can be about 4:1, or about 3:1, or about 2:1, or about 1.5:1, or about 1:1, or about 1:1.5, or about 1:2, or about 1:2.5, or about 1:3, or about 1:4, or about 1:5.

The oral care composition described in the present invention is configured for applying on the gingival tissue, as well as other soft tissue (e.g. buccal mucosa) inside the oral cavity of a subject. It has been surprisingly discovered that an oral care composition having both an optimal viscosity and a good adhesion and retention efficacy provides a better sensory benefit to the users, and also is particularly useful for promoting Gum Health benefits to users.

The oral care composition described therein is a leave-on composition. The leave-on composition is applied to the gingival tissue, e.g. gumline area, and left on for more than 2 minutes, preferably more than 10 minutes, more preferably more than 30 minutes and more preferably 60 minutes or longer. Preferably, the leave-on composition is applied to the gingival tissue as the last step of oral hygiene regimen. For example, the leave-on composition of the present invention is applied after brushing teeth, and optionally after using mouth rinse and/or floss.

In one aspect, the present invention is directed to an oral care composition which is in a gel form. It is desirable to have a gel for use in the present invention that enables easy application, thin layer formation and evenly spread into gingival sulcus/pockets and along gingival gum line. The oral care composition has a Viscosity Consistency Coefficient K of about 20 Pa·s to about 500 Pa·s, as measured by the Rheological Test method described herein. Preferably, the oral care composition has a Viscosity Consistency Coefficient K of about 20 Pa·s to about 500 Pa·s, preferably from about 30 Pa·s to about 400 Pa·s, more preferably from about 40 Pa·s to about 300 Pa·s, even more preferably from 50 Pa·s to 250 Pa·s. This optimal viscosity profile range provides better sensory experience of spread ability for a user. If a product is too viscous, it would be hard for a user to spread it evenly onto gingival tissue. If the product has a too low viscosity, it is runny and hard to be retained on appropriate area by finger or applicator. Alternatively, the oral composition can be applied in retained within the use of mouth tray/guard.

In one aspect, the oral care composition of present invention has a desirable mucoadhesion property. Mucoadhesion can be defined as adhesive interaction between two surfaces where one is at least mucosa for a given period through interfacial forces with a consequent decreased in the surface energy. Mucoadhesion polymers for oral care application should ideally (1) easily retain hydrophilic and lipophilic active ingredients and not hinder their release; (2) promote active ingredient penetration and absorption, (3) adhere as quickly as possible to biological substrate and be retained for a period of time, (4) be safe, (5) be cost effective and (6) provide user acceptable application.

The oral care composition of present invention has a Mucoadhesion Index in the range of not less than 0.3 FI %, as measured by the Mucoadhesion Test Method described herein. Preferably, the oral care composition has a Mucoadhesion Index of no less than about 0.5 FI %, and more preferably no less than about 1.0 FI %.

Fluoride

The oral care composition can comprise fluoride. The fluoride can be provided by a fluoride ion source. The fluoride ion source can comprise one or more fluoride containing compounds, such as stannous fluoride, sodium fluoride, potassium fluoride, amine fluoride, sodium monofluorophosphate, zinc fluoride, and/or mixtures thereof.

The fluoride ion source and the tin ion source can be the same compound, such as for example, stannous fluoride, which can generate tin ions and fluoride ions. Additionally, the fluoride ion source and the tin ion source can be separate compounds, such as when the tin ion source is stannous chloride and the fluoride ion source is sodium monofluorophosphate or sodium fluoride.

The fluoride ion source and the zinc ion source can be the same compound, such as for example, zinc fluoride, which can generate zinc ions and fluoride ions. Additionally, the fluoride ion source and the zinc ion source can be separate compounds, such as when the zinc ion source is zinc phosphate and the fluoride ion source is stannous fluoride.

The oral care composition can comprise a fluoride ion source capable of providing from about 50 ppm to about 3500 ppm, and preferably from about 500 ppm to about 3000 ppm of free fluoride ions. To deliver the desired amount of fluoride ions, the fluoride ion source may be present in the total oral care composition at an amount of from about 0.0025% to about 5%, from about 0.2% to about 1%, from about 0.5% to about 1.5%, or from about 0.3% to about 0.6%, by weight of the oral care composition.

Other Ingredients

The term "orally acceptable carrier" as used herein means a liquid or semi-solid vehicle such as a paste or a gel for containing the active ingredients of the present invention and delivering them to the oral cavity. Water is commonly used as a carrier material in oral compositions due to its many benefits. For example, water is useful as a processing aid, is benign to the oral cavity and assists in quick foaming of toothpastes. Water may be added as an ingredient in its own or it may be present as a carrier in other common raw materials such as, for example, sorbitol and sodium lauryl sulphate. The term total water content as used herein means the total amount of water present in the oral care composition, whether added separately or as a solvent or carrier for other raw materials but excluding that which may be present as water of crystallization in certain inorganic salts.

The oral care composition of the present invention comprises at least about 30% of a total water content. Preferably, the oral care composition comprises from more than about 35% to about 85% of a total water content. In other embodiments, the compositions include from about 40% to about 80%, alternatively from about 45% to about 75%, alternatively from about 50% to about 70%, alternatively from about 50% to about 60%, alternatively from about 45% to about 55%, alternatively from about 55% to about 65%, alternatively from about 65% to about 75%, alternatively combinations thereof, of a total water content.

The oral care compositions described herein may contain humectants. The humectants serve to keep the oral care composition from hardening upon exposure to air, to give a moist feel to the mouth, and, for particular humectants, to impart a desirable sweetness of flavor.

Suitable humectants for the present invention include edible polyhydric alcohols such as glycerin, sorbitol, xylitol, erythritol, butylene glycol, polyethylene glycol, propylene glycol, and combinations thereof. In one embodiment, the humectant is selected from sorbitol, glycerin, and combinations thereof. In another embodiment, the humectant is glycerin. In yet another embodiment, the humectant is sorbitol. In one embodiment, the oral care composition comprises from about 1% to less than about 50% of humectants by weight of the composition, preferably from about 10% to about 40%. In yet another embodiment, the oral care composition contains from about 15% to about 30% of glycerin by weight of the oral care composition.

In one example, the oral care composition of the present invention is substantially free of ethanol, preferably essentially free of ethanol. Ethanol is not desirable, in some cases, as it may cause irritating feeling to the users.

Preferably, the oral care composition of the present invention is substantially free of abrasives. The term "abrasive", for the purpose of present invention, includes calcium-containing abrasives and silica abrasives. The calcium-containing abrasives may be selected from the group consisting of calcium carbonate, dicalcium phosphate, tricalcium phosphate, calcium orthophosphate, calcium metaphosphate, calcium polyphosphate, calcium oxyapatite, sodium carbonate, and combinations thereof. In one embodiment where the calcium-containing abrasive is calcium carbonate, the calcium carbonate can be selected from the group consisting of fine ground natural chalk, ground calcium carbonate, precipitated calcium carbonate, and combinations thereof. The silica abrasives may generally have an average particle size ranging from 0.1 to 30 μm, and preferably from 5 to 15 μm. The silica abrasives can be precipitated silica or silica gels such as the silica xerogels marketed under the trade name "Syloid" by the W.R. Grace & Company, Davison Chemical Division and precipitated silica materials such as those marketed by the J.M. Huber Corporation under the trade name, Zeodent®, particularly the silicas carrying the designation Zeodent® 119, Zeodent® 118, Zeodent® 109 and Zeodent® 129.

Preferably, the oral care composition of the present invention contains low levels of abrasives. For example, the oral care composition may comprise from 0% to about 5% by weight of the composition, of abrasives, alternatively from 0% to about 3%, alternatively from 0% to about 2%, alternatively from 0% to about 1%, alternatively less than about 3%, or less than about 2%, or less than about 1%, or less than about 0.5%, by weight of the composition. Preferably, the composition is substantially free of the abrasives, more preferably free of the abrasives.

The oral care compositions herein may include from about 0.001% to about 5%, alternatively from about 0.01% to about 4%, alternatively from about 0.1% to about 3%, alternatively from about 0.5% to about 2%, alternatively combination thereof, of a flavorant composition by weight of the oral care composition. The term flavorant composition is used in the broadest sense to include flavor ingredients, or sensates, or sensate agents, or combinations thereof. Flavor ingredients may include those described in U.S. Publication No. 2012/0082630A1 at paragraph 39; and sensates and sensate ingredients may include those described at paragraphs 40-45, incorporated herein by reference.

Examples of flavor compositions or flavor ingredients include: mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, a-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, a-terpineol, linalool, limonene, citral, neral, geranial, geraniol nerol, maltol, ethyl maltol, anethole, dihydroanethole, carvone, menthone, beta-damascenone, ionone, gamma-decalactone, gamma-nonalactone, y-undecalactone, or combinations thereof. Generally suitable flavor ingredients are chemicals with structural features and functional groups that are less prone to redox reactions. These include derivatives of flavor ingredients that are saturated or contain stable aromatic rings or ester groups.

Sensates such as cooling, warming, and tingling agents are useful to deliver signals to the users. The most well-known cooling agent is menthol, particularly 1-menthol, which is found naturally in peppermint oil. Among synthetic cooling agents, many are derivatives of or are structurally related to menthol, i.e., containing the cyclohexane moiety, and derivatized with functional groups including carboxamide, ketal, ester, ether and alcohol. Examples include the p-menthanecarboxamide compounds such as N-ethyl-p-menthan-3-carboxamide (known commercially as "WS-3"). An example of a synthetic carboxamide cooling agent that is structurally unrelated to menthol is N,2,3-trimethyl-2-isopropylbutanamide. Additional exemplary synthetic cooling agents include alcohol derivatives such as 3-1-menthoxy-propane-1,2-diol, isopulegol, p-menthane-3,8-diol; menthone glycerine acetal (known commercially as "MGA"); menthyl esters such as menthyl acetate, menthyl acetoacetate, menthyl lactate, and monomenthyl succinate.

Additional agents that are structurally unrelated to menthol but have been reported to have a similar physiological cooling effect include alpha-keto enamine derivatives described in U.S. Pat. No. 6,592,884, including 3-methyl-2-(1-pyrrolidinyl)-2-cyclopenten-1-one (3-MPC), 5-methyl-2-(1-pyrrolidinyl)-2-cyclopenten-1-one (5-MPC); 2,5-dimethyl-4-(1-pyrrolidinyl)-3 (2H)-furanone (DMPF); icilin (also known as AG-3-5, chemical name 142-hydroxyphenyl]-4-[2-nitrophenyl]-1,2,3,6-tetrahydropyrimidine-2-one).

Some examples of warming agents include ethanol; nicotinate esters, such as benzyl nicotinate; polyhydric alcohols; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof.

Examples of some tingling agents include capsaicin; homocapsaicin, jambu oleoresin, zanthoxylum peperitum, saanshool-I, saanshool II, sanshoamide, piperine, piperidine, spilanthol, 4-(1-methoxymethyl)-2-phenyl-1,3-dioxolane, or combinations thereof.

The oral care compositions herein can further include herbal ingredients such as extracts of chamomile, oak bark, melissa, rosemary and salvia. These, and some of the herb-derived flavoring components can be included at levels just sufficient to provide a contribution to the flavor or they can be added at higher levels, such as 1% or more, in order to provide a greater therapeutic effect.

The oral care composition of the present invention may comprise preservatives. The preservatives may be benzyl alcohol, phenoxyethanol, sorbitan caprylate (Velsan SC®), 1-2 hexanediol & caprylyl glycol (Symdiol 68°), parabens and or combinations. The paraben may comprise methyl paraben or propyl paraben or combination thereof. Levels of benzyl alcohol or phenoxyethanol may be present at the amount of from greater than about 0.10% to about 0.40%, preferably about 0.15% to about 0.30%, and/or more preferably about 0.15% to about 0.20%. The levels of Velsan C® may be present at the amount of from about 0.10% to about 0.50%, preferably from about 0.20% to about 0.40%, more preferably alternatively from about 0.25% to about 0.30%. The level of Symdiol 68® may be present from about 0.10% to about 0.80%, preferably from about 0.10% to about 0.50% and more preferably about 0.20% to about 0.30%. Levels of paraben may be present at the amount of about 0.01% to about 0.20%, preferably about 0.02% to about 0.15%, more preferably about 0.05% to about 0.10%, by weight of the composition.

In one embodiment, the oral care compositions of the present invention are substantially free of triclosan (i.e., 5-chloro-2-(2,4-dichlorophenoxy)phenol), preferably free of triclosan.

The oral care compositions herein may include a sweetening agent. These include sweeteners such as saccharin, dextrose, sucrose, lactose, xylitol, maltose, levulose, aspartame, sodium cyclamate, D-tryptophan, dihydrochalcones, acesulfame, sucralose, neotame, and mixtures thereof. Sweetening agents are generally used in oral care compositions at levels of from about 0.005% to about 5%, alternatively about 0.01% to about 1%, by weight of the composition, alternatively from about 0.1% to about 0.5%, alternatively combinations thereof.

The oral care compositions herein may include a coloring agent (i.e., pigments, dyes and opacifiers). The coloring agent may be in the form of an aqueous solution, preferably 1% coloring agent in a solution of water. Titanium dioxide may also be added to the present oral care composition. Titanium dioxide is a white powder which adds opacity to the oral care compositions. Titanium dioxide generally comprises from about 0.25% to about 5%, by weight of the composition. It will be appreciated that selected components for the compositions must be chemically and physically compatible with one another.

The oral care compositions may include an effective amount of an anti-calculus agent, which in one embodiment may be present from about 0.05% to about 50%, alternatively from about 0.75% to about 25%, alternatively from about 0.1% to about 15%. Non-limiting examples include those described in U.S. Publication No. 2011/0104081A1 at paragraph 64, and those described in U.S. Publication No. 2012/0014883A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably from about 0.01% to about 2%, more preferably from about 0.1% to about 1% of the pyrophosphate salt by weight of the composition. Without wishing to be bound by theory, TSPP may provide not only calcium chelating thereby mitigating plaque formation, but also may also provide the additional benefit of monofluorophosphate stabilization (in those formulations containing monofluorophosphate).

The ingredients may provide additional benefits to the oral care composition. The use of extracellular antioxidants, e.g. ascorbate or α-tocopherol, as chain breaking or radical scavenging antioxidants, helps control and modulate the intracellular reactive oxygen species (ROS) that can cause host-tissue damage. The use of dexpanthenol can improve epithelialization and induce the proliferation phase in the wound healing of damaged tissue.

The present oral care composition may further comprise the usual and conventional ancillary components such as surfactants, anti-microbial agents, fluoride ions, and other ingredients that are known to one skilled in the art. It will be appreciated that selected components for the oral care compositions must be chemically and physically compatible with one another.

Method of Use

The present invention also relates to methods for treating the oral cavity comprising applying to the intraoral tissue (e.g. oral mucosa, gingiva) of the oral cavity of a subject, particularly the gum tissue, leaving on for more than 2 minute, preferably more than 10 minutes, more preferably more than 30 minutes, or more than 60 minutes or longer. The method of use herein comprises contacting a subject's oral mucosa (e.g. gingival margin or gingival sulcus/pockets) with the oral care composition according to the present invention.

The present invention further relates to a method of improving Gum Health of a subject using the oral care composition described herein comprising the step of applying the oral care composition onto the intraoral tissue of a subject, preferably applying along the gingival margin or sulcus at least once a day, preferably at least twice a day, more preferably every time immediately after brushing teeth. The term "immediately" herein means within 1 hour, preferably within 30 minutes, more preferably within 15 minutes, alternatively within 10 minutes.

The oral care composition can be applied onto the intraoral tissue of a subject by using an applicator, which applicator has a handle and a head, to spread the oral care composition along the gingival margin or sulcus of the subject. Preferably, the oral care composition is applied on the head of the applicator before being applied onto the intraoral tissue.

To further increase residence contact time between the oral gingiva and the oral care composition, then the oral composition can first be can be applied into a mouth guard tray, which is then placed into the mouth for upper, lower or both and worn preferably more than 30 minutes, or more than 60 minutes or longer and more preferably overnight.

The present invention further relates to a method of improving Gum Health of a subject, comprising at least two steps: (a) brushing teeth with an antibacterial toothpaste, preferably a stannous containing toothpaste, and immediately followed by (b) applying the oral are composition as defined herein onto the intraoral tissue of a subject, preferably applying along the gingival margin, sulcus or pockets.

The present invention further relates to a method of improving Gum Health of a subject, comprising at least two steps: (a) directing a user to apply a dentifrice composition to an oral cavity, and followed by (b) directing the user to apply an oral care composition comprising retinoid compound, as described herein, onto the intraoral tissue of a subject, preferably applying along the gingival margin, sulcus or pockets. The dentifrice composition can comprise a metal ion source, such as a tin, zinc, or combinations thereof, and/or fluoride. The oral care composition can comprise amino acid and/or mucoadhesive polymer. The oral care composition can also be a leave-on oral care composition to increase the contact time to more effectively deliver the retinoid compound to the gingival margin.

The direction to apply certain composition can be provided by an oral health professional, such as a dentist or a dental hygienist, and/or provided by directions listed on packaging materials for either composition or a kit including both compositions.

In practicing the present invention, the patient applies the oral care composition, as described herein, that contains the retinoid compound to obtain the desired effect, such as, treating gum recession, to the oral cavity. The composition can be applied with a paint-on device, a syringe or unit dose syringe, squeezable tube, a brush, a pen or brush tip applicator, a doe's foot applicator, swab, lip gloss applicator, strip that is removed after application, tray that is removed after application, or the like, or even with the fingers. The composition can also be combined with a delivery carrier, such as a strip of material, a dental tray, or a sponge material, and thereafter applied to the oral cavity. In certain embodiments, the compositions or delivery systems herein are almost unnoticeable when applied to oral cavity. After a desired period of time has elapsed, any residual composition may be easily removed by wiping, brushing or rinsing the oral surface. Alternatively, the residual composition can be left in place contacting the oral surface, indefinitely.

Dental tray appliances may be used as follows. The patient or dental professional dispenses the present composition into a soft or rigid dental appliance and then the participant places the appliance over the participant's dental arch (or fits the device around his or her teeth to keep the tray in position). Generally, the recommended treatment period is a sufficient period of time to achieve the benefit, as described herein. At the end of the treatment period, the dental appliance is removed, cleaned with water to remove any remaining composition, and then stored until the next application.

The described compositions and delivery systems, described herein, may be combined in a kit which comprises: 1. present composition and 2. instructions for use; or which comprises: 1. present composition, 2. instructions for use, and 3. a delivery carrier.

Delivery Carrier

The present invention may further be related to a delivery system or methods for delivering the oral care composition directly to the oral cavity or to the gingiva in the oral cavity of a consumer. The oral care composition can be used in combination with a re-usable delivery carrier, such as a tray, applicator, mouth guard, retainer, or combinations thereof. As the delivery carrier may be re-usable, it is desirable for the oral care composition to be rinseable or water-dispersible, as described herein. The oral care compositions can also be used in combination with a disposable or single-use delivery carrier, such as a disposable strip.

For example, the delivery system may comprise a first layer of a carrier material and a second layer comprising an oral care composition described herein, whereby the retinoid compound and/or amino acid is releasably located within the present composition. A suitable first layer may comprise a delivery carrier including a strip of material, a dental tray, a sponge material, and mixtures thereof. In certain embodiments, the delivery carrier may be a strip of material, such as a permanently deformable strip. Suitable strips of material or permanently deformable strips are for example disclosed in U.S. Pat. Nos. 6,136,297; 6,096,328; 5,894,017; 5,891,453; and 5,879,691; and in U.S. Pat. Nos. 5,989,569 and 6,045,811; and in patent application US 2014/0178443 A1.

The delivery carrier may comprise a dissolvable film, such as the dissolvable film strip disclosed in U.S. Pat. No. 6,709,671, herein incorporated by reference, which can be adhered to the oral cavity thereby releasing an active, the dissolvable film comprising water-soluble polymers, one or more polyalcohols, and one or more actives. In addition to one or more actives, a dissolvable film may contain a combination of certain plasticizers or surfactants, colorants, sweetening agents, flavors, flavor enhancers, or other excipients commonly used to modify the taste of formulations intended for application to the oral cavity. The resulting dissolvable film is characterized by an instant wettability which causes the dissolvable film to soften soon after application to the mucosal tissue, thus preventing the patient from experiencing any prolonged adverse feeling in the mouth, and a tensile strength suitable for normal coating, cutting, slitting, and packaging operations.

The dissolvable film may comprise a water-soluble polymer or a combination of water-soluble polymers, one or more plasticizers or surfactants, one or more polyalcohols, and an active. The polymers used for the dissolvable film include polymers which are hydrophilic and/or water-dispersible. Examples of polymers that can be used include polymers that are water-soluble cellulose-derivatives, such as hydroxypropylmethyl cellulose, hydroxyethyl cellulose, or hydroxypropyl cellulose, either alone, or mixtures thereof. Other optional polymers, without limiting the invention, include polyvinyl pyrrolidone, carboxymethyl cellulose, polyvinyl alcohol, sodium alginate, polyethylene glycol, natural gums like xanthan gum, tragacantha, guar gum, acacia gum, arabic gum, water-dispersible polyacrylates like polyacrylic acid, methylmethacrylate copolymer, carboxyvinyl copolymers. The concentration of the water-soluble polymer in the final film can very between 20 and 75% (w/w), or between 50 and 75% (w/w).

The strip of material may contain shallow pockets. When the multi-phase oral care composition is coated on a strip of material, bleach agents and/or oral care actives, fill shallow pockets to provide reservoirs of additional bleach agents and/or oral care actives. Additionally, the shallow pockets help to provide texture to the delivery system. The strip of material may have an array of shallow pockets. Generally, the shallow pockets are approximately 0.4 mm across and about 0.1 mm deep. When shallow pockets are included in the strip of material and multi-phase oral care compositions herein are applied to it in various thicknesses, in certain embodiments the overall thickness of the delivery system is less than about 1 mm, in certain embodiments the overall thickness is less than about 0.5 mm.

The delivery systems as used herein may comprise an adhesion means, such that they are capable of adhesion to oral surfaces, especially the teeth. This adhesion means may be provided by the present compositions herein or the adhesion means may be provided independently of the compositions herein (for example the adhesion means is a separate phase from the compositions herein where the compositions may also have an adhesive means). The strip of material may be held in place on the oral surface by adhesive attachment provided by the present composition. The viscosity and general tackiness of the multi-phase oral care composition to dry surfaces may cause the strip to be adhesively attached to the oral surface without substantial slippage from the frictional forces created by the lips, teeth, tongue, and other oral surfaces rubbing against the strip of material while talking drinking, etc. However, this adhesion to the oral surface may be low enough to allow the strip of material to be easily removed by the wearer by simply peeling off the strip of material using one's finger. The delivery system may be easily removable from the oral surfaces without the use of an instrument, a chemical solvent or agent or excess friction.

In addition, the strip of material may be held in place on the oral surface by adhesive means and attachment provided by the delivery carrier itself. For example, the strip of material can extend, attach, and adhere to the oral soft tissue. In addition, an adhesive can be applied to that portion of the strip of material that will attach the delivery systems to the oral soft tissue. The delivery carrier may also be attached to the oral cavity by physical interference or mechanical interlocking between the delivery carrier and the oral surfaces including the teeth. In addition, the strip of material may be held in place by an adhesion means that is independent of the composition of the present inventions herein, as disclosed in WO 03/015656.

Suitable adhesion means are known to the skilled person. When the adhesive means, if present, is provided by an adhesive, the adhesive may be any adhesive which may be used to adhere materials to the tooth surface or to a surface of the oral cavity surfaces. Suitable adhesives include, but are not limited to, skin, gum and muco adhesives, and should be able to withstand the moisture, chemicals and enzymes of the oral environment for long enough for the oral care actives and/or bleach to take effect, but may be soluble and/or biodegradable thereafter. Suitable adhesives may for example comprise water soluble polymers, hydrophobic and/or non-water-soluble polymers, pressure and moisture sensitive adhesives, e.g. dry adhesives which become tacky upon contact with the mouth environment, e.g. under the influence of moisture, chemicals or enzymes etc. in the mouth. Suitable adhesives include natural gums, synthetic resins, natural or synthetic rubbers, those gums and polymers listed above under "Thickening Agents", and various other tacky substances of the kind used in known adhesive tapes, those known from U.S. Pat. No. 2,835,628.

In addition, the delivery system may comprise an optional release liner. Such a release liner may be formed from any material which exhibits less affinity for the second layer composition than the second layer composition exhibits for itself and for the first layer strip of material. The release liner may comprise a rigid sheet of material such as polyethylene, paper, polyester, or other material, which is then coated with a nonstick type material. The release liner may be cut to substantially the same size and shape as the strip of material or the release liner may be cut larger than the strip of material to provide a readily accessible means for separating the material from the strip. The release liner may be formed from a brittle material that cracks when the strip is flexed or from multiple pieces of material or a scored piece of material. Alternatively, the release liner may be in two overlapping pieces such as a typical adhesive bandage design. A description of materials suitable as release agents is found in Kirk-Othmer, Encyclopedia of Chemical Technology, Fourth Edition, Volume 21, pp. 207-218, incorporated herein by reference.

The delivery carrier may be a permanently deformable strip of material having a yield point and thickness such that the strip of material substantially conforms to a shape of a tooth via permanent deformation under a pressure less than about 250,000 Pascals as it has been found that wearers will press a strip onto each tooth using one fingertip having about one square centimeter surface area. They typically apply force at each tooth for one second or less with a typical application pressure ranging from about 100,000 Pascals to about 250,000 Pascals.

The strip of material can have visco-elastic properties which enable it to creep as well as bend in order to conform across several teeth and around the arch of the wearer's mouth. It is important that the necessary permanent deformation occurs under minimum normal force being applied by the wearer.

The deformable strip of material may be made of a permanently deformable material, such as wax, putty, tin or foil, as a single layer or a combination of layers or materials, such as a laminate. In certain embodiments, the deformable strip may be wax, such as #165 sheet wax formulated and manufactured by Freeman Mfg. & Supply Co. of Cleveland, Ohio. This particular wax readily conforms to the shape of a tooth under a pressure of about 133,000 Pascal which is the pressure generated when the wearer applies a normal force of about 3 pounds (1.36 kg) over an area of about one square centimeter. The deformable strip of material may have a nominal film thickness of about 0.8 mm, wherein the deformable strip may be substantially flat and rectangular in shape with rounded corners. The deformable strip of material may have a length sufficient to cover a plurality of adjacent teeth while conforming to the curvature of the wearer's mouth and gaps between the adjacent teeth. If the deformable strip of material includes the multi-phase oral care composition coated thereon, the multi-phase oral care composition may have an overall thickness less than about 1.5 mm. Deformable strips as disclosed herein may also be used as the material for the strip of material 12 shown in FIGS. 1 to 4. Thus, general features of a strip of material as described above for example with respect to FIGS. 1 to 4 may also apply to the deformable strip of material. In addition, a release liner and/or shallow pockets may also be combined with a deformable strip of material.

The present compositions may be used in combination with a delivery carrier including a dental tray and/or foam material. Suitable dental trays include rigid appliances, oversized rigid custom dental appliances rigid bilaminated custom dental appliances, disposable soft foam trays.

A rigid appliance which is fitted precisely to the patient's dental arches. For example, an alginate impression which registers all teeth surfaces plus gingival margin is made and a cast is promptly made of the impression. An "oversized" rigid custom dental appliance. The fabrication of rigid, custom dental appliances entails fabricating cast models of the patient's dental arch impressions, and heating and vacuum-forming a thermoplastic sheet to correspond to the cast models of a patient's dental arches. A third type of rigid custom dental appliance, used with less frequency, is a rigid bilaminated custom dental appliance fabricated from laminations of materials, ranging from soft porous foams to rigid, non-porous films. The non-porous, rigid thermoplastic shells of these bilaminated dental appliances encase and support an internal layer of soft porous foam.

Disposable U-shaped soft foam trays can be individually packaged, and which may be saturated with a pre-measured quantity of the composition of the present invention. The soft foam material is generally an open celled plastic material. Such a device is commercially available from Cadco Dental Products in Oxnard, Calif. under the tradename VitalWhite™.

In certain embodiments, the tray may have pockets built into the surface covering or contacting one or more teeth. Such pockets may help hold the oral composition in contact with the teeth. In certain embodiments, the pockets may be from about 0.05 to about 5 mm deep, preferably from about 0.1 to about 3 mm deep, more preferably from about 0.3 to about 3 mm deep, or most preferably from about 0.5 to about 1.5 mm deep. Examples of such trays include those specified in the Clinical Protocol section.

In certain embodiments, the fit of the tray to the oral cavity may have a tolerance or gap built into it on the oral cavity. Such as tolerance or gap may help hold the oral composition in contact with the oral cavity. In certain embodiments, the tolerance or gap may be from about 0.01 mm to about 2 mm, preferably from about 0.05 mm to about 1 mm, more preferably from about 0.1 mm to about 1 mm, or most preferably from about 0.1 mm to about 0.5 mm.

Packaging Materials for Compositions

An oral care product can be sold including the leave-on oral care composition. The oral care product can include primary packaging, such as a tube, bottle, and/or tub. The primary package can be placed within secondary package, such as a carton, shrink wrap, or the like. The oral care product can include a primary package, but be free of a secondary package to reduce materials used.

Instructions for use of the oral care composition can be printed on the primary package and/or the secondary package. The user can be instructed to dispense the leave-on oral care composition from the tube.

The primary and/or secondary packaging can be made from material that are sustainable, recyclable, compostable, and/or disintegrable. The tube can be made entirely from materials that can be recyclable in commercial and/or municipal recycling streams. The user can be instructed to place the primary packaging, such as a tube, and/or the secondary packaging, such as a carton, directly into a home recycling container to be picked up by a recycling service, and/or into a store-hosted collected receptacle. Suitable materials that can be recyclable include paper, cardboard paper, corrugated cardboard, polyethene, such as low density polyethylene, medium density polyethylene, and/or high density polyethylene, polyethylene terephthalate, polyvinyl chloride, aluminum, glass, polypropylene, polystyrene, and/or combinations thereof. The primary and/or secondary packaging can be made from a single material, such as high density polyethylene, so that commercial and/or municipal recycling streams are not poisoned with another material that can be difficult to remove.

The primary and/or secondary packaging can include metal foil. Alternatively, the primal), and/or secondary packaging can be free of a metal foil, so that the primary and/or secondary packaging can be suitable to recycle without contaminating the recycling stream with a metal foil, which may be recyclable in a separate recyclable stream and/or non-recyclable.

Product Forms

As described herein, the oral care composition can be a leave-on oral care composition to increase the contact time between the retinoid compound and/or amino acid/peptide with the gingiva. Suitable product forms include a gel composition comprising mucoadhesive polymer, a dispersion of retinoid compound and/or amino acid/peptide in a hydrophobic composition, an oil-in-water emulsion composition, a water-in-oil emulsion composition, a jammed oil-in-water emulsion composition, a jammed water-in-oil emulsion composition, or combinations thereof. These product forms can be utilized with or without a delivery carrier.

Gel compositions can be aqueous compositions and include mucoadhesive polymer, as described herein.

Oral dispersion compositions are disclosed in U.S. Patent Application Publication No. 2020/0330341, which is herein incorporated by reference in its entirety. The oral dispersion can include hydrophilic particles, such as the disclosed retinoid compound and/or amino acid/peptide, dispersed in a liquid or semisolid hydrophobic phase. The hydrophobic phase can include petrolatum, mineral oil, or combinations thereof. The oral dispersion can comprise from about 50% to about 99%, from about 60% to about 99%, at least about 50%, at least about 60%, or at least about 75%, by weight of the oral dispersion, of the hydrophobic phase.

Emulsion compositions are disclosed in U.S. Patent Application Publication No. 2018/0133122, which is herein incorporated by reference in its entirety. The emulsion composition can include an aqueous phase, a hydrophobic phase, retinoid compound, and amino acid/peptide. The retinoid compound and/or amino acid/peptide can be in the aqueous phase. The emulsion composition can include from about 0.01% to about 20%, from about 0.1% to about 15%, or from about 1% to about 15%, by weight of the emulsion composition, of the aqueous phase. The emulsion composition can also include a hydrophobic phase. Suitable hydrophobic phase can include petrolatum, mineral oil, coconut oil, or combinations thereof. The oral care composition can include from about 50% to about 99%, from about 60% to about 99%, at least about 50%, at least about 60%, or at least about 75%, by weight of the emulsion, of the hydrophobic phase.

For water-in-oil emulsions comprising retinoid compound and/or amino acid/peptide, it has been surprisingly found that the size of the droplets of the aqueous phase is a factor to decrease oral/topical irritation. Without being bound by theory, if the size of the droplets of the aqueous phase is too large it may lead to large spots on oral/topical/tooth surfaces that are exposed to a high concentration of the retinoid compound and/or amino acid/peptide, which in turn may lead to oral/topical irritation and/or tooth-sensitivity. The emulsion composition can have a number-average equivalent-diameter or volume-average equivalent-diameter of the droplets of aqueous phase of no more than about 0.001 micron, 0.01 micron, 0.1 micron, 1 micron, 5 microns, 10 microns, 50 microns, 100 microns, 500 microns, and/or 1000 microns. The emulsion composition can also have number-average equivalent-diameter or volume-average equivalent-diameter of the droplets of aqueous phase of from about 0.001 micron to about 1000 microns, preferably from about 0.01 micron to about 1000 microns, more preferably from about 0.1 micron to about 100 microns, and most preferably from about 1 to about 100 microns or any other numerical range.

Jammed oil-in-water emulsion compositions are disclosed in U.S. Pat. No. 11,096,874, which is herein incorporated by reference in its entirety. The term, "jammed emulsion" as used herein, is a high internal phase emulsion 1) wherein the high internal phase emulsion exhibits no more than 5% macroscopic separation after 48 hours at 23° C. measured according to the method specified herein, and/or 2) wherein separate regions of discontinuous phase influence the shape of one another. Examples of jammed emulsions may include high internal phase emulsions in which adjacent or neighboring regions of discontinuous phase influence the shape of one another.

The jammed oil-in-water emulsion compound can be structured in manner such that the aqueous phase becomes a thin continuous phase between distinct regions of the hydrophobic phase (referred to as a jammed oil-in-water emulsion). In certain aspects of jammed oil-in-water emulsions, the hydrophilic or aqueous phase is the minor component and the hydrophobic phase, despite being the discontinuous phase, is the major component. Microscopically, regions of continuous aqueous phase appear as a thin continuous phase surrounding discrete hydrophobic regions. Jammed oil-in-water emulsions have several advantages over traditional oil-in-water emulsions. For example, in a traditional oil-in-water emulsion, a minority discontinuous hydrophobic phase is stabilized in a majority continuous aqueous phase. Delivering an active agent, such as a retinoid compound and/or amino acid/peptide, from a majority continuous aqueous phase can lead to tooth sensitivity and gum irritation when using the high concentrations of active agent(s) needed to reduce gum recession.

Surprisingly, as described herein, it was found that by adding the predominant hydrophobic phase to the less predominant hydrophilic phase, a jammed oil-in-water emulsion can be prepared. It is counter intuitive to add the major hydrophobic component to the minor hydrophilic component. The jammed emulsion can be prepared by adding a portion of the hydrophobic phase to the hydrophilic phase followed by mixing and then repeating the procedure until all of the hydrophobic phase has been added to the hydrophilic phase.

Without not wishing to be bound by theory it was surprisingly found that active agent can be effective in very overall low concentrations, but high in local concentration, if presented in a multi-phase oral care composition as disclosed herein. The jammed oil-in-water emulsion can include from about 0.01% to about 25%, from about 1% to about 20%, from about 2.5% to about 20%, or preferably from about 5% to about 15%, by weight or volume of the jammed oil-in-water emulsion, of the aqueous phase. The jammed oil-in-water emulsion can comprise from about 75% to about 99%, from about 80% to about 97.5%, greater than about 80%, greater than about 90%, or preferably, from about 85% to about 95%, by weight or volume of the jammed oil-in-water emulsion, of the hydrophobic phase. The hydrophobic phase can comprise a non-toxic oil, such as non-toxic edible oil. The hydrophobic phase can comprise non-toxic edible oils, saturated or unsaturated fatty alcohols, aliphatic hydrocarbons, long chain triglycerides, fatty esters, and combinations thereof. The hydrophobic phase may also comprise silicones, polysiloxanes, and mixtures thereof. The hydrophobic phase may be preferably selected from mineral oil, petrolatum, coconut oil, and combinations thereof.

The jammed oil-in-water emulsion, as described herein, can comprise from about 0.001% to about 20%, from about 0.01% to about 10%, up to about 10%, up to about 5%, or from about 0.1% to about 10%, by weight of the jammed oil-in-water emulsion, of the emulsifier.

Classes of surfactants useful as emulsifiers include nonionic surfactant, anionic surfactant, cationic surfactant, zwitterionic surfactant, amphoteric surfactant, polymeric surfactant, synthetic surfactant, and/or combinations thereof. Many suitable nonionic and amphoteric surfactants are disclosed by U.S. Pat. Nos. 3,988,433; 4,051,234, and many suitable nonionic surfactants are also disclosed by U.S. Pat. No. 3,959,458.

The emulsifier can comprise polysorbate, an alkyl sulfate, Lipowax® D, or combinations thereof. Suitable polysorbate compounds include, polysorbate 20, 40, 60, 80, or combinations thereof, such as Tween® 20, 40, 60, 80, or combinations thereof.

The HLB values of various emulsifiers and/or blends of multiple emulsifiers can be from about are from about 0 to about 60, above 11, from about 11 to about 60, from about 11 to about 40, preferably from about 11 to about 20, or more preferred from about 16 to about 18, or combinations thereof; or from about 20 to about 40, or from about 30 to about 40. The emulsifier or blend of multiple emulsifiers can be hydrophilic, miscible with water, immiscible with mineral oil, or combinations thereof.

Other suitable compositions for the delivery of the retinoid compound and/or amino acid include unit-dose compositions, such as the unit-dose compositions of U.S. Patent Application Publication No. 2019/0343732, which is herein incorporated by reference in its entirety, dentifrice compositions, mouth rinse compositions, mouthwash compositions, tooth gel, subgingival gel, mouth rinse, mousse, foam, mouth spray, lozenge, chewable tablet, chewing gum, tooth whitening strips, floss and floss coatings, breath freshening dissolvable strips, denture care products, denture adhesive products, or combinations thereof.

Examples

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

TABLE 1

| Compositions | | | |
|---|---|---|---|
| Ingredients | Ex. 1 Comparative | Ex. 2 Inventive | Ex. 3 Inventive |
| Glycerin | 20.000 | 20.000 | 20.000 |
| Xylitol | 2.000 | 2.000 | 2.000 |
| PEG 300 | 0.500 | 0.500 | 0.500 |
| Mucoadhesive Polymers (Carbomer, PVPK90, Hyaluronate) | 3.526 | 3.526 | 3.526 |
| Sodium PEG-7 Olive Oil Carboxylate (Olivem ® 400) | — | — | 0.17 |
| Retinol | — | 0.15 | 0.15 |
| pal-KTTKS [SEQ ID NO. 2] peptide | — | 0.003 | 0.003 |
| Sodium Hyaluronate | 0.500 | 0.500 | 0.500 |
| Sodium Pyrophosphate | 0.500 | 0.500 | 0.500 |
| Sodium Hydroxide (50%) | 0.900 | 0.900 | 0.900 |
| Preservatives | 0.150 | 0.150 | 0.150 |
| Flavorant | 1.030 | 1.030 | 1.030 |
| Sodium Saccharin | 0.100 | 0.100 | 0.100 |
| Water and minors (e.g. coloring agent) | Q.S. | Q.S. | Q.S. |

TABLE 1 shows the compositions tested. Example 1 is a comparative example of a gel composition and does not include retinoid compound, peptide, or olive oil. Example 2 is the same gel composition of Example 1, but includes retinoid compound (retinol) and peptide (pal-KTTKS [SEQ ID NO. 2] peptide), but does not include olive oil. Example 3 is the same gel composition of Example 1 and Example 2, but includes retinoid compound (retinol), peptide (pal-KTTKS [SEQ ID NO. 2] peptide), and olive oil (Olivem® 400).

In-Vitro 3D Full-Thickness Gingival Tissue Model Assay

In-vitro gingival 3D tissue was used to assess the effects of treatment with Inventive Compositions and Comparative Compositions on histology and immune chemistry.

The initial preparation of the full-thickness gingival tissue model (GIN-300-FT, available from MatTek, US) was similar with methods previously described to produce other full thickness tissue models (Delvenne et al., 2001; Odioso et al., 1995). Briefly, 1 mL of serum containing $1*10^6$ gingival fibroblasts was mixed with a collagen solution to form a fibroblast-collagen gel matrix. The mixture was allowed to gelatinize by incubating the inserts at 37° C. for 1 h. The gel was then equilibrated with 2 mL of growth medium and cultured for 48 h. Thereafter, autologous gingival epithelial cells were seeded atop the matrix and the tissue was cultured in incubator at 37° C. with 5% $CO_2$ for 2-3 weeks until stratum corneum at apical layer is observed, resulting in a multilayered in vitro human gingival culture derived from primary human gingival epithelial cells and fibroblasts.

Inventive Compositions and Comparative Compositions were diluted in sterile water to a 10% concentration, then the 10% slurries were sterile filtered by passing through filters with a pore size of 0.22 μL. 100 μL of each filtered 10% slurry was added to the apical side of the tissue. Tissues were cultured for 48 hours in incubator at 37° C. with 5% $CO_2$.

Histology and Immunohistochemical Analysis

To examine the morphology of the in vitro reconstructed tissues, inserts containing tissues were fixed with 10% formalin, embedded in paraffin, and 5-7 μm thick cross-sections were cut. The sections were mounted on microscopic slides, stained with hematoxylin and eosin (H&E, available from Sigma, US), and observed and photographed using a Nikon Diaphot microscope outfitted with a CoolPix 990 digital camera.

Tissues were fixed in Carnoy's fixative solution (acetic acid:ethanol:chloroform, 10:60:30) overnight at 4° C., embedded in paraffin, and sectioned for routine histology. Sections were deparaffinized and rehydrated. Endogenous peroxide was blocked using 1% $H_2O_2$/Tris buffered saline (TBS). After blocking with 3% normal serum of the source of secondary biotinylated antibody, the sections were incubated with primary antibodies. Detection was via the avidin-biotin-peroxidase complex method using diaminobenzidene as substrate. A p-value cutoff of 0.05 or less was considered statistically significant. The antibodies used were Collagen 1, Collagen 4, Collagen 6, Laminin-5, Hyaluronic Acid, Tropelastin, Aquaporin-7, MMP-1, and β-galactosidase, as shown in TABLE 2.

TABLE 2

| Antibodies | | | |
|---|---|---|---|
| Target | 1° antibody | Cat# | Company |
| Collagen 1 | Collagen I alpha 1 antibody | NBP1-82488 | Novus Biologicals |
| Collagen 4 | Anti-Collagen IV antibody | ab6586 | Abcam |
| Collagen 6 | Anti-Collagen VI antibody | ab180855 | Abcam |

TABLE 2-continued

| Antibodies | | | |
|---|---|---|---|
| Target | 1° antibody | Cat# | Company |
| Laminin-5 | Anti-Laminin 5 antibody | ab14509 | Abcam |
| Hyaluronic Acid | Biotinylated HABP | AMS.HKD-BC41 | Amsbio |
| Tropoelastin | Anti-Tropoelastin antibody | Ab21600 | Abcam |
| Aquaporin-7 | Aquaporin 7 Polyclonal Antibody | 25131-1-AP | Thermo Fisher Scientific |
| MMP-1 | Anti-MMP1 antibody | ab52631 | Abcam |
| β-Galactosidase | Anti-GLB1/Beta-galactosidase antibody | ab203749 | Abcam |

TABLE 3

| 3D full-thickness gingival tissue model assay | | | | |
|---|---|---|---|---|
| | Measure Marker | Ex. 1 | Ex. 2 | Ex. 3 |
| Epidermal | Epithelia Thickness (um) | 199 | 218 | 243 |
| | Actin (A.U.) | 3184 | 4504 | 5607 |
| | Aquaporin-7 (A.U.) | 16892 | 26602 | 43422 |
| | β-Galactosidase (A.U.) | 4349 | 3391 | 2171 |
| | Matrix Metalloproteinase 1 (A.U.) | 53741 | 37935 | 18519 |
| Dermal-Epidermal Junction | Laminin-5 (A.U.) | 2219 | 2511 | 2840 |
| Dermal | Hyaluronic Acid (A.U.) | 6771 | 12430 | 21520 |
| | Collagen 1 (A.U.) | 2646 | 6151 | 9642 |
| | Collagen 4 (A.U.) | 2723 | 7783 | 14864 |
| | Collagen 6 (A.U.) | 2040 | 3688 | 9698 |
| | Trepoelastin (A.U.) | 1632 | 2595 | 2871 |
| | β-Galactosidase (A.U.) | 14016 | 13912 | 11462 |

TABLE 3 shows the impact of the addition of retinoid compound, peptide, and olive oil on the gingiva. The 3D full-thickness gingival tissue model assay shows the biological structure mechanisms that can be influenced. Example 1, a comparative composition, included only a mucoadhesive polymer, hyaluronic acid, which has been previously proposed to provide gum health benefits. Example 2, an inventive composition, included hyaluronic acid, retinol, and pal-KTTKS [SEQ ID NO. 2] (a pentapeptide). Example 2 showed an increase in collagen regulation and a decrease in matrix metalloproteinase (MMP) regulation. Additionally, the thickness of the epithelia increased from 199 μm to 218 μm. Thus, in total, the addition of retinol and pentapeptide led to the increase in epithelia layer tissue growth.

Example 3, an inventive composition, included hyaluronic acid, retinol, pal-KTTKS [SEQ ID NO. 2] (a pentapeptide), and olive oil (Olivem® 400). Example 3 showed an additional increase in collagen regulation and an additional decrease in matrix metalloproteinase (MMP) regulation relative to Example 2, which did not include olive oil. Additionally, the thickness of the epithelia increased from 199 μm (Example 1) to 218 μm (Example 2) to 243 μm (Example 3). While not wishing to being bound by theory, it is believed that the use of the olive oil, such as Olivem® 400, can enhance the penetration and delivery of the retinoid compound and/or the amino acid/peptide into the epidermal and dermal layers of the gum tissue in the oral cavity. While not wishing to being bound by theory, it is believed that the use of the olive oil, such as Olivem® 400, can also act as a source for the building blocks of healthy cell membranes. In total, the addition of olive oil, such as olive oil reacted with ethylene glycol, to a leave-on oral care composition including retinoid compound and/or amino acid/peptide can reduce prevent gingival recession, increase gum resilience, stop gingival recession, reverse gingival recession, promote collagen synthesis, promote fibrillin synthesis, or combinations thereof in an oral cavity of a user of the leave-on oral care composition.

In-Vitro 2D Tissue Damage Assay Via Collagen-1 Marker

In vitro gingival 2D gingival fibroblast tissue damage/prevention was used to assess the effects of treatment with Inventive Compositions and Comparative compositions on collagen-1 ELISA assay.

Primary Human Gingival Fibroblast (HGF) Cell Culture, Maintenance:

The obtained tissues were kept in cold Dulbecco's modified Eagle's medium (DMEM, Gibco) with 10% fetal bovine serum and a cocktail of antibiotics and antimycotics. Next, the tissues were minced with a blade and spun down at 4° C. and 200×g for 5-10 minutes to separate and wash the pellets. Resuspended tissue explants were laid onto a 60 mm dish and kept in an incubator. Every 3-5 days during culture, fibroblasts grown from tissue explants were washed and continued under passage using 0.2% trypsin. Proliferation tests and cell damage recovery experiments were performed when the fibroblasts reached passages 3-10.

Primary Human gingival fibroblast (HGF) cell was maintained in a 37° C. incubator with 5% $CO_2$ saturation. Dulbecco's modified Eagle's medium (DMEM, Gibco) containing 10% fetal calf serum, 1% penicillin-streptomycin was used as the complete culture medium, which was changed every 2-3 days.

Ageing Tissue Degradation Reactive Oxygen Species Challenge $2\times10^5$ cells were seeded in 6-well plate and cultured with complete medium in at 37° C. and 5% $CO_2$ for 24 h. The cells were treated with 2 mL 0.5% RP gel dilution after reaching 40-60% confluency and incubated for 24 hr (37° C., 5% $CO_2$, 95% RH). The complete medium was removed, and cells were washed three time with PBS.

Then 2 mL medium with 50 μM tert-butyl hydroperoxide (TBHP) was added to cells and incubated for 1 hr at 37° C., 5% $CO_2$ and 95% RH. 2',7'-Dichlorodihydrofluorescein diacetate (DCFH-DA) stock solutions was diluted into PBS (1:1000) to make 10 μM working solution. The TBHP medium was removed and the cell was washed 3 times with PBS. Cells were incubated with 1 mL of 10 μM DCFH-DA solution for 30 min at 37° C. and 5% $CO_2$. The medium was removed and washed 3 times with PBS. The cells were harvested by trypsinization and washed once with PBS. Cells were suspended in 400 μL PBS and submitted to flow cytometry for ROS detection using the 488 nm laser for excitation and detected at 525 nm.

Collagen-1 ELISA Analysis:

$1.8\times10^5$ Cells were seeded in a 6-well plate and cultured with complete medium in at 37° C. and 5% $CO_2$ for 24 hr. The cells were treated with 2 mL 0.5% RP gel dilution after reaching 40-60% confluency and incubated for 24 hr (at 37° C., 5% $CO_2$ and 95% RH). The medium was removed and the cells were washed three times with PBS, then 2 mL medium with 50 μM TBHP was added to cells and incubated for 1 hr at 37° C., 5% $CO_2$ and 95% RH. The TBHP medium was removed and the cells were washed three times with PBS. The cells were incubated in complete media for 24 hr at 37° C., 5% $CO_2$ and 95% RH. The supernatant of cell culture was collected and analysed by Collagen-1 ELISA kit (CUSABIO). The results of the Collagen-1 ELISA kit are shown in TABLE 4.

TABLE 4

| Collagen-1 Marker | | | |
|---|---|---|---|
| Treatment | | Collagen-1 (ng/ml) | |
| Control | Untreated Control | 74.49 | — |
| Control | Positive control (TGF-B) | 155.59 | — |
| Ex 1a | Retinol solubilized in polysorbate-20 (1500 ppm) Pal-KTTKS [SEQ ID NO. 2] Peptide (30 ppm) | 138.20 | 23% |
| Ex 1b | Retinol solubilized in polysorbate-20 (1500 ppm) Pal-KTTKS [SEQ ID NO. 2] Peptide (30 ppm) + Sodium PEG-7 Olive Oil Carboxylate (1700 ppm) | 211.54 | |
| Ex 2a | Retinol solubilized in Caprylic/ CapricTriglyceride (1500 ppm) Pal-KTTKS [SEQ ID NO. 2] Peptide (30 ppm) | 163.42 | 26% |
| Ex 2b | Retinol solubilized in Caprylic/ CapricTriglyceride (1500 ppm) Pal-KTTKS [SEQ ID NO. 2] Peptide (30 ppm) + Sodium PEG-7 Olive Oil Carboxylate (1700 ppm) | 219.97 | |
| Ex. 3a | Retinol solubilized in Glycine Soja (1500 ppm) Pal-KTTKDS Peptide (30 ppm) | 151.22 | 42% |
| Ex 3b | Retinol solubilized in Glycine Soja (1500 ppm) Pal-KTTKDS Peptide (30 ppm) + Sodium PEG-7 Olive Oil Carboxylate (1700 ppm) | 262.62 | |

TABLE 4 demonstrates the benefit of the addition of olive oil, such as Olivem® 400 (Sodium PEG-7 Olive Oil Carboxylate), to increase the penetration of retinol into gingival tissue. In each case, the addition of Sodium PEG-7 Olive Oil Carboxylate (Ex. 1a, 2a, and 3a) increased the regulation of collagen relative to a positive control and relative to an identical composition without Sodium PEG-7 Olive Oil Carboxylate (Ex. 1b, 2b, and 3b), which also included other emulsifiers that are normally used to solubilize retinol. In each case, Sodium PEG-7 Olive Oil Carboxylate increase the regulation of collagen.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

SEQUENCE LISTING

```
Sequence total quantity: 3
SEQ ID NO: 1             moltype = AA  length = 4
FEATURE                  Location/Qualifiers
REGION                   1..4
                         note = Peptide E
source                   1..4
                         mol_type = protein
                         organism = synthetic construct
SEQUENCE: 1
RSRK                                                                    4

SEQ ID NO: 2             moltype = AA  length = 5
FEATURE                  Location/Qualifiers
REGION                   1..5
                         note = pal-KTTKS
source                   1..5
                         mol_type = protein
                         organism = synthetic construct
SEQUENCE: 2
KTTKS                                                                   5

SEQ ID NO: 3             moltype = AA  length = 4
FEATURE                  Location/Qualifiers
REGION                   1..4
                         note = GEKG
source                   1..4
                         mol_type = protein
                         organism = synthetic construct
SEQUENCE: 3
GEKG                                                                    4
```

The invention claimed is:

1. A leave-on oral care composition comprising:

(a) about 0.01% to about 2%, by weight of the composition, of retinoid compound;

(b) about 0.0001% to about 5%, by weight of the composition, of peptide selected from glycine-histidine-lysine, glycine-glutamic acid-lysine-glycine, lysine-threonine-threonine-lysine-serine, and combinations thereof;

(c) about 0.01% to about 5%, by weight of the composition, of PEGylated olive oil, wherein the PEGylated olive oil comprises a product of a reaction between olive oil and ethylene oxide; and (d) a fluoride source, wherein the leave-on oral care composition is an emulsion composition and has a yield stress of about 2 Pa to about 250 Pa at 23° C.

2. The leave-on oral care composition of claim 1, wherein the PEGylated olive oil comprises PEGylated olive oil triglyceride, PEGylated olive oil diglyceride, PEGylated olive oil monoglyceride, PEGylated olive oil fatty acid, or combinations thereof.

3. The leave-on oral care composition of claim 1, wherein the PEGylated olive oil comprises PEG olive oil carboxylic acid, a salt thereof, or a mixture thereof, and the PEG olive oil carboxylic acid comprises sodium PEG-n olive oil carboxylate and n is a number from about 4 to about 20.

4. The leave-on oral care composition of claim 3, wherein the PEG olive oil carboxylic acid comprises sodium PEG-7 olive oil carboxylate.

5. The leave-on oral care composition of claim 1, wherein the retinoid compound comprises retinol, retinyl ester, retinal, retinoic acid, tocopheryl-retinoate, tocopherol ester of cis-or trans-retinoic acid, isotretinoin, alitretinoin, etretinate, acitretin, adapalene, bexarotene, tazarotene, or combinations thereof.

6. The leave-on oral care composition of claim 5, wherein the retinoid compound comprises the retinyl ester, and the retinyl ester comprises retinyl palmitate, retinyl acetate, retinyl propionate, or combinations thereof.

7. The leave-on oral care composition of claim 1, wherein the peptide comprises a pentapeptide covalently bonded to an aliphatic chain, and the pentapeptide has the sequence of lysine-threonine-threonine-lysine-serine [SEQ ID NO. 2].

8. The leave-on oral care composition of claim 1, wherein the composition has a Viscosity Consistency Coefficient K of from 20 Pa's to 500 Pas as measured at 22° C. at a shear rate range of 0.1-10_s-1 and a Mucoadhesion Index of no less than 0.3 Fluorescent Intensity Percentage ("FI %").

9. The leave-on oral care composition of claim 1, wherein the composition comprises mucoadhesive polymer, and the mucoadhesive polymer comprises polyacrylic acid, natural gum, linear sulfated polysaccharide, anionic cellulose, non-ionic cellulose derivative, polyvinyl pyrrolidine, hyaluronic acid, or combinations thereof.

10. The leave-on oral care composition of claim 1, further comprising metal ion source, and the metal ion source comprises tin, zinc, copper, or combinations thereof.

11. The leave-on oral care composition of claim 1, further comprising gum strengthening polyol, and the gum strengthening polyol comprises isomalt, maltitol, lactitol, maltotriitol, maltotetraitol, polyglycitol, or combinations thereof.

12. A leave-on oral care composition comprising:

(a) about 0.01% to about 2%, by weight of the composition, of retinol;

(b) about 0.0001% to about 1%, by weight of the composition, of lysine-threonine-threonine-lysine-serine;

(c) about 0.01% to about 1%, by weight of the composition, of PEG-7 olive oil carboxylate or a salt thereof; and (d) at least about 30% water, by weight of the composition, wherein the composition in in the form of a gel having a Viscosity Consistency Coefficient K of 20 Pa's to 500 Pa's as measured at 22° C. at a shear rate range of 0.1-10 s-1 and a Mucoadhesion Index of no less than 0.3 Fluorescent Intensity Percentage.

13. The leave-on oral care composition of claim 12, further comprising a mucoadhesive polymer comprising a polyacrylic acid (PAA) and an additional polymer at a weight ratio of PAA to additional polymer of about 5:1 to 1:5.

14. A method of improving gum health of a user, comprising:

applying the oral care composition of claim 1 to gum tissue of the user; and leaving the oral care composition on the gum tissue for more than 2 minutes, wherein the oral care composition provides a gum health benefit.

15. The method of claim 14, wherein the composition is left on the gum tissue for more than 10 minutes.

16. The method of claim 14, wherein the composition is applied to the gum tissue with a delivery carrier selected from a tray, an applicator, a mouth guard, a retainer, or a film strip.

17. The method of claim 14, further comprising brushing teeth prior to applying the oral care composition to the gum tissue.

* * * * *